(12) United States Patent
Kopparapu

(10) Patent No.: US 10,748,040 B2
(45) Date of Patent: Aug. 18, 2020

(54) SYSTEM AND METHOD FOR AUTOMATIC ASSESSMENT OF CANCER

(71) Applicant: Kavya Venkata Kota Sai Kopparapu, Herndon, VA (US)

(72) Inventor: Kavya Venkata Kota Sai Kopparapu, Herndon, VA (US)

( * ) Notice: Subject to any disclaimer, the term of this patent is extended or adjusted under 35 U.S.C. 154(b) by 117 days.

(21) Appl. No.: 16/193,828

(22) Filed: Nov. 16, 2018

(65) Prior Publication Data

US 2019/0156159 A1 May 23, 2019

Related U.S. Application Data

(60) Provisional application No. 62/588,651, filed on Nov. 20, 2017.

(51) Int. Cl.
*G06K 9/00* (2006.01)
*B41M 5/00* (2006.01)
(Continued)

(52) U.S. Cl.
CPC ....... *G06K 9/6267* (2013.01); *G06K 9/00147* (2013.01); *G06K 9/4628* (2013.01); *G06K 9/6269* (2013.01); *G06K 9/6273* (2013.01); *G06K 9/6276* (2013.01); *G06K 9/6278* (2013.01); *G06K 9/66* (2013.01); *G06T 7/0012* (2013.01); *G16B 20/00* (2019.02); *G16B 25/00* (2019.02); *G16B 40/00* (2019.02); *G16B 40/20* (2019.02); *G16H 30/20* (2018.01); *G06T 2207/10056* (2013.01);
(Continued)

(58) Field of Classification Search
USPC ....... 382/100, 103, 106, 128–133, 156, 159, 382/162, 168, 173, 181, 199, 219, 222, 382/254, 274, 276, 291, 305, 312, 157; 378/21, 140, 28
See application file for complete search history.

(56) References Cited

U.S. PATENT DOCUMENTS

2016/0210403 A1* 7/2016 Zhang .................. G16B 25/00
2017/0145513 A1* 5/2017 Kennedy ............ A61B 10/0096
(Continued)

OTHER PUBLICATIONS

Han & Kamber, Chapter 6, "Data Mining, Concepts and Techniques," 2nd Ed. Elsevier: Amsterdam, 2006, pp. 285-382.
(Continued)

*Primary Examiner* — Seyed H Azarian
(74) *Attorney, Agent, or Firm* — Hunton Andrews Kurth LLP

(57) ABSTRACT

Glioblastoma multiforme (GBM) is the most aggressive type of brain cancer. It is critical to determine the most effective patient-specific treatment quickly. Exemplary embodiments use a data-driven approach to extracting brain tumor information from data obtain from Whole Slide Image that is uploaded through an interface. Exemplary embodiments generate the following information about a glioblastoma tumor from a brain biopsy slide using neural networks: annotated areas of relevant tissues, molecular subtype, and expression status of an important gene and include three steps: the segmentation of tumor features; prediction of molecular subtype; and prediction of gene methylation status from a WSI.

17 Claims, 27 Drawing Sheets
(16 of 27 Drawing Sheet(s) Filed in Color)

(51) Int. Cl.

| | |
|---|---|
| *G06K 9/62* | (2006.01) |
| *G06T 7/00* | (2017.01) |
| *G06K 9/66* | (2006.01) |
| *G16H 30/20* | (2018.01) |
| *G16B 25/00* | (2019.01) |
| *G16B 40/00* | (2019.01) |
| *G16B 20/00* | (2019.01) |
| *G06K 9/46* | (2006.01) |
| *G16B 40/20* | (2019.01) |

(52) U.S. Cl.
CPC ............... *G06T 2207/20081* (2013.01); *G06T 2207/20084* (2013.01); *G06T 2207/30016* (2013.01); *G06T 2207/30024* (2013.01); *G06T 2207/30096* (2013.01)

(56) References Cited

U.S. PATENT DOCUMENTS

| | | | | |
|---|---|---|---|---|
| 2018/0341745 | A1* | 11/2018 | Zhang | G16B 50/00 |
| 2018/0374210 | A1* | 12/2018 | Barker | G06T 7/0012 |
| 2019/0276897 | A1* | 9/2019 | Donovan | C12Q 1/6886 |

OTHER PUBLICATIONS

LeCun et al., "Convolutional Networks for Images, Speech, and Time-Series," in M.A. Arbib, editor, The Handbook of Brain Theory and Neural Networks, MIT Press, 1995, pp. 1-14.

Beckett, J., Brainiac vs. Brain Cancer: Teen Tackles Deadly Disease. (NVIDIA Blog, Mar. 2018) Retrieved from https://blogs.nvidia.com/blog/2018/03/15/teen-uses-ai-to-tackle-brain-cancer/, pp. 1-3.

Bejnordi, et al., Health Sciences, Deep Learning-Based Assessment of Tumor-Associated Stroma for Diagnosing Cancer in Histopathology Images, Feb. 19, 2017, pp. 1-5.

Brain Tumor Statistics. (n.d.). Retrieved from American Brain Tumor Association, website: http://www.abta.org/about-us/news/brain-tumor-statistics/, Dec. 5, 2017, pp. 1-2.

Brown, S., Northwestern University, "The Science and Application of Hematoxylin and Eosin Staining," Retrieved from http://mhpl.facilities.northwestern.edu/files/2013/10/The-Science-and-Application-of-Hematoxylin-and-Eosin-Staining-6-5-2012, 2012, pp. 1-92.

Caffe: Deep Learning Framework by Berkeley AI Research. (n.d.), Retrieved from http://caffe.berkeleyvision.org/, Dec. 5, 2017, pp. 1-4.

Christians, et al., PLOS One, "Prognostic Value of Three Different Methods of MGMT Promoter Methylation Analysis in a Prospective Trial on Newly Diagnosed Glioblastoma," Mar. 2012, vol. 7, Issue 3, pp. 1-9.

Cornish, T. Johns Hopkins, "An Introduction to Digital Whole Slide Imaging and Whole Slide Image Analysis," Retrieved from http://www.hopkinsmedicine.org/mcp/PHENOCORE/CoursePDFs/2013/13/2019/20Cornish/20Digital/20Path.pdf, Jul. 19, 2013, pp. 1-17.

Dana Farber Cancer Institute, "How We Diagnose Brain Tumors," Retrieved from http://www.dana-farber.org/brain-tumors/diagnosis/, Dec. 5, 2017, pp. 1-6.

Kopparapu, K., Davidson Institute—2018 Davidson Fellows, "GlioVision: A Platform for the Automatic Assessment of Glioblastoma Tumor Features, Molecular Identity, and Gene Methylation from Histopathological Images Using Deep Learning," Retrieved from https://www.davidsongifted.org/Fellows-Scholarship/2018-Davidson-Fellows/Kavya-Kopparapu-Laureate, pp. 1-30.

Deng, J., et al., IEE Computer Vision and Pattern Recognition, "ImageNet: A Large-Scale Hierarchical Image Database," 2009, pp. 1-9.

Ertosun, M., et al., AMIA annual symposium proceedings, Automated Grading of Gliomas Using Deep Learning in Digital Pathology Images: A Modular Approach with Ensemble of Convolutional Neural Networks, 2015, pp. 1898-1908.

Fawcett, T., Pattern Recognition Letters, "An Introduction to ROC Analysis," 27, 2006, pp. 861-874.

"FDA allows marketing of first whole slide imaging system for digital pathology." (2017), Retrieved from Food and Drug Administration Press Announcements website: https://www.fda.gov/newsevents/newsroom/pressannouncements/ucm552742.htm, pp. 1-2.

Gandomkar, Z., et al., Journal of Pathology Informatics, Computer-Based Image Analysis in Breast Pathology, Oct. 21, 2016, pp. 1-12.

Glioblastoma Multiformem, (n.d.), Retrieved from American Association of Neurological Surgeons, website: http://www.aans.org/Patients/ Neurosurgical-Conditions-andTreatments/Glioblastoma-Multiforme, 2017, pp. 1-6.

Heinrich, G., "Image Segmentation Using Digits 5," Retrieved from NVIDIA Blogs, website: https://devblogs.nvidia.com/parallelforall/image-segmentation-using-digits-5/, Nov. 10, 2016, pp. 1-22.

Homeyer, A., et al., Computerized Medical Imaging and Graphics, "Practical Quantification of Necrosis in Histological Whole-Slide Images," 2013, pp. 313-322.

Hou et al., Computer Vision Foundation, Patch-based Convolutional Neural Network for Whole Slide Tissue Image Classification. ar Xiv., 2016, pp. 2424-2433.

ImageNet Large Scale Visual Recognition Competition, "ImageNet Large Scale Visual Recognition Challenge (ILSVRC)," Retrieved from http://www.image-net.org/challenges/LSVRC/, Dec. 7, 2017, pp. 1-2.

"Improve Neural Network Generalization and Avoid Overfitting" (n.d.). Retrieved from Mathworks website: https://www.mathworks.com/help/nnet/ug/improve-neural-network-generalization-and-avoid-overfitting.html, Dec. 5, 2017, pp. 1-8.

Ivy Glioblastoma Atlas Project. (n.d.). Retrieved from Allen Brain Institute: IVYGAP website: http://glioblastoma.alleninstitute.org/, Dec. 5, 2017, pp. 1-2.

Kwon et al., PLOS One, "Recurrent Glioblastomas Reveal Molecular Subtypes Associated with Mechanistic Implications of Drug-Resistance," 2015, pp. 1-16.

Krizhevsky et al., Neural Information Processing Systems Conference Proceedings, ImageNet Classification With Deep Convolutional Neural Networks, 2012, pp. 1-11.

Kursa, M., et al., Journal of Statistical Software, "Feature Selection with the Boruta Algorithm," Retrieved from https://www.rdocumentation.org/packages/Boruta/versions/5.2.0/topics/Boruta, Sep. 2010, vol. 36, Issue 11, pp. 1-13.

Levner et al., Medical Image Computing and Computer-Assisted Intervention, "Predicting MGMT Methylation Status of Glioblastomas from MRI Texture," 2009, pp. 522-530.

Litjens, G. et al., Nature Scientific Reports, "Deep Learning as a Tool for Increased Accuracy and Efficiency of Histopathological Diagnosis," May 23, 2016, pp. 1-11.

Long, J., et al., IEEE Computer Vision and Pattern Recognition Conference Proceedings, Fully Convolutional Networks for Semantic Segmentation, Mar. 2015, pp. 1-10.

Lundh, F., Python Imaging Library (PIL), Retrieved from Pythonware website: http://www.pythonware.com/products/pil/, Dec. 7, 2017, pp. 1-2.

Overview of TCGA. (n.d.), Retrieved from National Institutes of Health, "The Cancer Genome Atlas," website: https://cancergenome.nih.gov/abouttcga/overview, Dec. 7, 2017, pp. 1-2.

Parikh, R., et al., Indian Journal of Ophthalmol, "Understanding and Using Sensitivity, Specificity and Predictive Values," 2008, Jan.-Feb., 56(1): 45-50, pp. 1-18.

Ronneberger, O., et al., rXiv, "UNet: Convolutional Networks for Biomedical Image Segmentation," May 2015, pp. 1-8.

Shah et al., PLOS One, "Comprehensive Analysis of MGMT Promoter Methylation: Correlation With MGMT Expression and Clinical Response in GBM," Jan. 201, vol. 6, Issue 1, pp. 1-11.

Simonyan et al., ICLR Conference Proceedings, Very Deep Convolutional Networks for Large-Scale Image Recognition, 2015, pp. 1-14.

Cedoz et al., Stanford, "CS231n Final Report," Retrieved from http://cs231n.github.io/ transfer-learning/, 2017, pp. 4321-4327.

Stergiou et al. "Neural Networks," Retrieved from Imperial College of London, website: https://www.doc.ic.ac.uk/~nd/surprise_96/journal/vol4lcs11/report.html, Dec. 5, 2017, pp. 1-13.

(56) References Cited

OTHER PUBLICATIONS

Szegedy, et al., IEEe Computer Vision and Pattern Recognition and Pattern Recognition Conference Proceedings, "Going Deeper with Convolutions", 2015, pp. 1-9.

Taylor, T., et al., Curr Cancer Drug Targets, "Targeting EGFR for Treatment of Glioblastoma: Molecular Basis to Overcome Resistance," Mar. 2012, 12(3): 197-209, pp. 1-23.

Thon, N., et al., OncoTargets and Therapy, "Personalized Treatment Strategies in Glioblastoma: MGMT Promoter Methylation Status," Sep. 26, 2013, pp. 1361-1372.

Verhaak et al., Cander Cell, Integrated Genomic Analysis Identifies Clinically Relevant Subtypes of Glioblastoma Characterized by Abnormalities in PDGFRA, IDH1, EGFR, and NFI. 2010, 17, pp. 98-110.

Walid, M., The Permanente Journal, "Prognostic Factors for Long-Term Survival After Glioblastoma," Fall 2008, vol. 12, No. 4, pp. 45-48.

Wang, Y., et al., PLOS One, "SurfaceSlide: A Multitouch Digital Pathology Platform," Jan. 2012, vol. 7, Issue 1, pp. 1-12.

Zachark et al., Magnetic Renosance in Medicine, (2009), 62:1609-1618, Classification of Brain Tumor Type and Grade Using MRI Texture and Shape in a Machine Learning Scheme, pp. 1-10.

CS231n Convolutional Neural Networks for Visual Recognition, http://cs231n.github,io/transfer-learning, Dec. 7, 2017, pp. 1-3.

Kopparapu, K., "GlioVision: A Platform for the Automatic Assessment of Glioblastoma Tumor Features, Molecular Identity, and Gene Methylation, from Histopathological Images Using Deep Learning," 2017, pp. 1-22.

YouTube Video link, Kopparapu, Ted Talks, Harnessing the Power of Artificial Intelligence to Diagnose Diseases, https://www.youtube.com/watch?v=kLx4ey4d8DQ, May 2017.

YouTube Video link, Kopparapu, Biden Cancer Summit, https://www.youtube.com/watch?v=k75S_-P6CKY, 2018.

\* cited by examiner

200

| Region | Description | Color |
|---|---|---|
| Leading Edge (LE) | Outermost boundary of tumor; tumor/normal cell ration ~ 1/100 | |
| Infiltrating Tumor (IT) | Intermediate between LE and CT, tumor/normal cell ratio ~ 10/100 | |
| Cellular Tumor (CT) | Major part of core, tumor/normal cell ratio ~500/1. Cell density varies due to edema or necrosis | |
| Necrosis (NE) | Found in core of tumor, signified by dead or dying tissue with disintegrating nuclei. | |
| Psudopalisading Cells (CTpan) | Found in core of tumor surrounding NE regions, tumor cells aggregate in 10-30 nuclei wide rows of higher density pointing towards NE | |
| Perinecrotic Zone (CTpnz) | Found in the core of tumor, formed boundary of tumor cells along edge of NE without demarcation of CTpan | |
| Hyperplastic Blood Vessels (HBV) | Found throughout tumors, marked by increased density of blood vessels with thickened walls (endothelial cell proliferation) | |

FIG. 2A

| | Classical | Mesenchymal | Proneural | Neural |
|---|---|---|---|---|
| Genetic Changes | • Chromosome 7 Amplification<br>• Chromosome 10 Deletion<br>• High-level EGFR amplification | • Deletions in NF1<br>• High expression of CHI3L1 and MET gene | • Alterations of PDGFRA gene<br>• Point mutation in IDH1<br>• TP53 mutation | • Expression of neuron markers such as NEFL, GABRA1, SYT1 and SLC12A5 |
| Clinical Correlations | • Murine astrocytic cell progenitors | • Higher overall necrosis and associated inflammatory infiltrate<br>• Astroglial cell progenitors | • Traditionally observed in younger patients<br>• Associated with secondary GBM<br>• Oligodendrocytic cell progenitors | • Associations with oligodendrocytic and astrocytic differentiation<br>• Strong correlation for genes differentially expressed by neurons |
| Treatment Implications | • Aggressive treatment reduces mortality | • Aggressive treatment reduces mortality | • Aggressive treatments did not affect mortality | • Aggressive treatments' highly likely to reduce mortality |

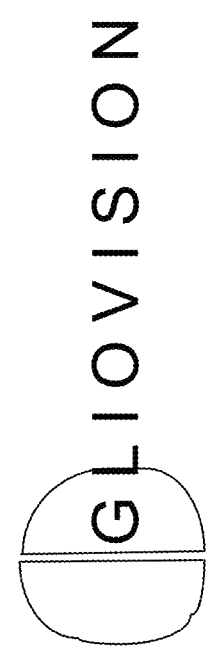

400

GLIOVISION  [HOME] [ABOUT THE PLATFORM]

GlioVision the first platform for the automatic analysis of glioblastoma histopathological images to segment tumor regions with over 85% accuracy, predict molecular subtype with over 94% accuracy, and determine MGMT promoter methylation status with over 95% accuracy. Its innovative use of cutting-edge artificial intelligence technology enables high-accuracy alternatives to traditional glioblastoma diagnostic testing.

If you would like to find out more about the technology and methodology behind the system, visit the "About the Platoform" tab.

If you would like to analyze an H&E-stained whole slide image using the GlioVision system, upload the .svs file in the box below.

410

[Upload Image]     [Browse]

| Study | Brief Description | Input Data | Cancer Type | Samples | Methodology | Accuracy | Difference between GlioVision and Study |
|---|---|---|---|---|---|---|---|
| GlioVision | Tumor Features | | | | Fully Convolutional Network | | |
| | Molecular subtype | WSIs | Glioblastoma | 150+ WSIs | | 86.02% | |
| | MGMT methylation | | | | Convolutional Neural Network | 94.21% | |
| | | | | | | 96.00% | |
| Levner et al. | MGMT methylation status | MRIs | Glioblastoma | 59 MRIs | L1-regularized Neural Networks | 87.7% | Different input image, not as accurate |
| Cedoz et al. | DDB2 Gene Methylation | WSIs | Glioblastoma and Lower Grade Glioma | 28 WSIs | Convolutional Neural Networks | 84% | Different gene's methylation status, lower accuracy |
| Hou et al. | Discriminative region segmentation | WSIs | Non small Cell Lung Carcinoma | ~250 WSIs | Convolutional Neural Networks | 79.8% | Lower accuracy, Regions segmented (discriminative, diagnostic, other) not as specific |
| Homeyer et al. | Necrosis segmentation and quantification | WSIs | Not Specified | Not Specified | Naïve Bayes, k-Nearest Neighbor, Random Forest Classifiers | 86-90% | Only necrosis region segmented, different methodology |

| Algorithm | Train Loss | Val Loss | Val Accuracy | Patch-Level Results | | | | WSI-Level |
|---|---|---|---|---|---|---|---|---|
| | | | | Test Accuracy | AUROC | Sensitivity | Specificity | Test Accuracy |
| Feature Segmentation | 0.438 | 0.427 | 84.70% | 86.02% | | | | |
| Subtype Classification | 0.201 | 0.117 | 92.6% | 93.21% | Proneural: 0.999<br>Mesenchymal: 0.990<br>Neural: 0.993<br>Classical: 0.995 | 94.839%<br>93.846%<br>88.092%<br>96.154% | 99.843%<br>94.904%<br>99.221%<br>95.784% | 100% |
| MGMT Methylation Classification | 0.1023 | 0.0915 | 95.573% | 96.00% | 0.96 | 89.42% | 91.12% | 100% |

FIG. 20

SYSTEM AND METHOD FOR AUTOMATIC ASSESSMENT OF CANCER

CROSS-REFERENCE TO RELATED PATENT APPLICATIONS

This application claims priority to U.S. Provisional Application No. 62/588,651, filed Nov. 20, 2017, entitled "System and Method for Automatic Assessment of Cancer," the disclosure of which is herein incorporated by reference in its entirety.

FIELD OF THE INVENTION

The present disclosure relates generally to a method of treating a patient that has glioblastoma multiforme ("GBM"), also referred to as glioblastoma. Exemplary embodiments integrate multiple biological feature classifiers into a single platform to generate relevant genetic, molecular, and histopathological information from a Whole Slide Image ("WSI"), to detect and treat GBM as soon as possible. Other types of inputs may be used. Specifically, the disclosure relates to a platform that uses trained machine learning architecture, e.g., neural networks, and datasets of medical images, e.g., WSIs to extract relevant histopathological and genetic information to enable an oncologist and other professionals within the field to prescribe aggressive treatments with confidence in a timely manner. The disclosure relies on a tile-based image analysis approach. The tiles of interest are segmented as inputs, and the input WSIs are preprocessed using techniques such as tiling and cyclic pooling and trained with networks initialized via a transfer learning technique.

BACKGROUND OF THE INVENTION

GBM is the most common and aggressive malignant brain tumor among adults. Despite recent advances in neuroimaging, surgery, and drug therapies, the prognosis for patients diagnosed with GBM has not improved since the 1980s. Currently, treatments for determining GBM are based on time-consuming and costly manual tumor feature segmentation and genetic panel testing to determine molecular subtype and $O^6$-methylguanine methyltransferase ("MGMT") promoter methylation, both of which are implicated in chemotherapy effectiveness.

Using the approach of the prior art, patients have a mean survival time of 12 months post-diagnosis because the symptoms accompanying GBM are often non-specific, ranging from mild headaches and nausea to personality changes and other stroke-like symptoms, making early detection and treatment difficult. These and other deficiencies exist.

SUMMARY OF THE INVENTION

An exemplary embodiment includes using three network models in-step to assess GBM. The three network models include, first, a tumor feature segmentation, wherein a tumor is classified into relevant tumor and necrosis regions. Second, a tumor molecular subtype classification, wherein the cell tumor regions are classified into three subtypes: Classical, Mesenchymal, and Proneural. And third, an MGMT promoter methylation classification, wherein the MGMT gene is classified either MGMT+ or MGMT−. The three network models are trained with a combination of two separate datasets. After the MGMT gene is classified, a professional in the field prescribes effective treatment for the diagnosed GBM.

An objective of the present disclosure is to provide an accurate data-driven approach to extracting tumor information from a single brain biopsy image, using that information to prescribe treatment for the tumor.

A further objective of the present disclosure is to enable oncologists, neurologists, and other professionals in the field to prescribe appropriate treatment with confidence in a timely manner including decreased diagnosis time.

Another objective of the present disclosure is to automatically annotate the biopsy image to indicate the extent of tumor biological features, such as tumor proliferation, necrosis, and hyperplastic blood vessels in tissues, decreasing the workload of neuropathologists and other professionals in the field.

Another objective of the present disclosure is to predict the molecular subtype of the tumor, which is indicative of mutations in several important genes; and to predict the methylation status of the MGMT gene, a promoter region implicated in the chemotherapy effectiveness, which would render costly and time-consuming genetic testing unnecessary.

A further objective of the present disclosure is to present pathology images to predict the molecular signature of GBM tumors.

A still further objective of the present disclosure is to present an approach to predicting molecular information using a classification system, including but not limited to Fully Convolutional Networks ("FCN"), Convolutional Neural Networks ("CNN"), or an ensemble thereof.

In a further embodiment, a computer implemented method for characterization of a tumor may comprise: receiving, on at least one processor, data from a human subject with a brain tumor; evaluating, using the at least one processor, the data using a classifier which is an electronic representation of a classification system, each said classifier trained using an electronically stored set of training data vectors, each training data vector representing an individual human and data for the respective human, each training data vector further comprising a classification with respect to the characterization of the brain tumor in the respective human; and outputting, using the at least one processor, a classification of the sample from the human subject concerning the characterization of the brain tumor in the subject based on the evaluating step.

The classification system may be selected from the group consisting of machine learning and deep learning architectures, including support vector machines, genetic algorithms, penalized logistic regression, LASSO, ridge regression, naïve Bayes classifiers, classification trees, k-nearest neighbor classifiers, neural nets, elastic nets, Bayesian neural networks, Random Forests, gradient boosting trees, AdaBoost, Fully Convolutional Network (FCN), Convolutional Neural Network (CNN), or an ensemble thereof. The classification system may comprise Fully Convolutional Network (FCN), Convolutional Neural Network (CNN), or an ensemble thereof.

The characterization may comprise identification of the tumor as a GBM.

The characterization may comprise providing tumor features, MGMT methylation status, molecular subtype determination, and combinations thereof.

The data may comprise histopathological data, genetic information, or a combination thereof. The histopathological data may be obtained from a whole brain slide, preferably a scanned biopsy Whole Slide Image ("WSI") of a human brain of a subject having a brain tumor. The data may be processed by a tile-based image analysis framework, including tumor feature segmentation. The histopathological data may comprise leading edge (LE), infiltrating tumor (IT), cellular tumor (CT), perinectronic zone (CTpnz), necrosis (CTne), pseudopalisading cells (CTpan), hyperplastic blood vessels (hbv), or a combination thereof.

Exemplary embodiments may use a brain biopsy for the prediction of genetic, molecular, and histopathological information implicated in glioblastoma. However, it should be appreciated that other imaging techniques may be used, such as but not limited to, Magnetic Resonance Images (MRIs), Proton Emission Tomography (PET) scans, Computer Tomography (CT) scans, and X-Ray images. Thus, the exemplary embodiments which rely upon WSIs can also use data from these other imaging techniques.

The genetic information may comprise changes in EGFR, NF1, PDGFRA/IDH1, and neuronal genes, preferably mutations. The genetic information may comprise chromosome 7 ampliciation, chromosome 10 deletion, high-level EGFR amplification, deletions in NF1 gen, high expression of CH13L1 gene, high expression of MET gene, alternations of PDFRA gene, point mutations in IDH1, TP53 mutation, expression of neuron markers by astrocytes, O6-methylguanine-DNA methyltransferase (MGMT) methylation, or a combination thereof. The neuron markers may comprise NEFL, GABA Receptor α1, SYT1, SLC12A5.

The characterization may comprise identification of the tumor as a glioblastoma, and preferably further comprising molecular subtype classification as a Classical, Mesenchymal, Proneural, or Neural glioblastoma.

The characterization may comprise identification of the tumor as a glioblastoma and preferably further comprising that the glioblastoma is either MGMT+ or MGMT−.

The characterization may comprise identification of the tumor as a glioblastoma and preferably further comprise providing histopathological data that may comprise leading edge (LE), infiltrating tumor (IT), cellular tumor (CT), perinectronic zone (CTpnz), necrosis (CTne), pseudopalisading cells (CTpan), hyperplastic blood vessels (hbv), or a combination thereof.

The test data and each training data vector may further comprise at least one additional characteristic selected from the group consisting of the sex, age, genetic information, biomarker data, smoking status, or a combination thereof of the individual human.

A further embodiment includes a non-transitory computer readable medium having code to carry out the preceding method.

Another embodiment includes a system to carry out the preceding method. The system may including various components and different computer systems, including components that are physically separated and remote from one another. A first computer may be used to access a remotely located server on which the method according to exemplary embodiments is executed. The first computer may access the server through an interface, such as a web-based interface. The output of the method may be provided through the web-based interface. The method may be carried out over a computer based network, such as the Internet.

This and other embodiments and advantages will become apparent from the following detailed description, taken in conjunction with the accompanying drawings, illustrating by way of example, the principles of the various embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, the objectives and advantages thereof, reference is now made to the following descriptions taken in connection with the accompanying figures in which:

FIG. 2A depicts an example of seven annotated tumor regions in the IVY Glioblastoma Atlas Project ("IVYGAP") dataset, associated biological description, and annotated color.

FIG. 2C depicts a table describing four types of tumors.

FIG. 4A depicts a home page of a web application according to an exemplary embodiment.

FIG. 17 depicts an example of patches from the test set and associated MGMT methylation status predictions according to an exemplary embodiment.

FIG. 19 depicts information about several related studies and the differences between the studies and an exemplary embodiment.

FIG. 20 depicts the loss, accuracy, AUROC, sensitivity, and specificity results for each of the three classifiers, i.e., Classical, Mesenchymal, and Proneural according to an exemplary embodiment.

DETAILED DESCRIPTION OF PREFERRED EMBODIMENTS

Figure 1:
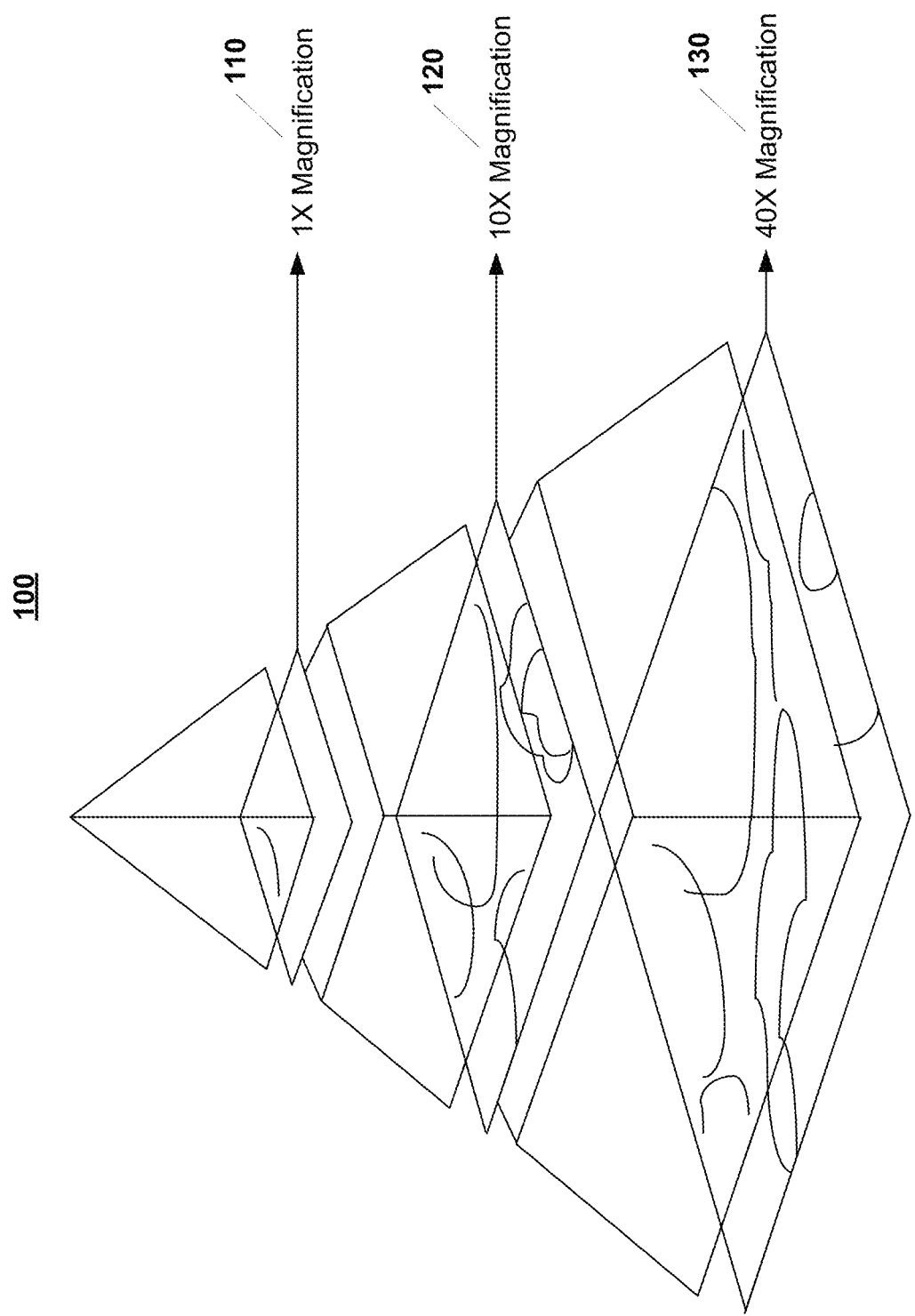
FIG. 1 depicts a WSI format with varying magnifications according to an exemplary embodiment.

The following description provides different configurations and features according to an exemplary embodiment. While certain nomenclature and types of applications and software are described, other names, and applications and software usage are possible. The nomenclature provided is done so by way of a non-limiting example. Further, while particular embodiments are described, it should be appreciated that the features and functions of each embodiment may be combined in any combination as is within the capability of one of ordinary skill in the art. The figures provide additional exemplary details regarding the present invention. It should also be appreciated that the following exemplary embodiment is provided as a non-limiting example only.

The following embodiment is exemplary because there are a variety of ways to carry out methods according to the present disclosure. The methods and systems depicted and described can be executed or otherwise performed by one or a combination of various systems and modules. Each block shown in the embodiment represents one or more processes, decisions, methods or subroutines carried out in the exemplary method, and these processes, decisions, methods or subroutines are not necessarily carried out in the specific order outlined in the methods, nor is each of them required.

Glioblastoma multiforme (herein referred to as GBM or glioblastoma) is the most common and aggressive malignant brain tumor among adults. Surgical removal of the entire tumor is almost impossible, and in most cases less than 90% can be removed. Glioblastoma are described by physicians as having finger-like tentacles that extend some distance from the main tumor mass into surrounding normal brain tissue. Unlike tumors in other parts of the body where a clear margin of normal tissue surrounding the tumor can often be taken to maximize the chances of complete tumor removal, this is generally not feasible for the brain where a balance has to be made between tumor removal and risks to cognitive function, or indeed immediate patient survival. If the GBM is left untreated, it can grow or metastasize to other areas in the brain. Another reason GBM are difficult to treat is that many drugs cannot efficiently cross the "blood-brain barrier" to enter the brain to act on the tumor. Further, glioblastomas are heterogeneous. Glioblastomas comprise various populations of cells, some of which respond to treatment and others which do not. These other cells linger and spread through the brain, resulting in little long-term success. See National Cancer Institute. These and other factors make GBM a pernicious and difficult tumor to characterize and treat.

The current treatment pipeline for GBM is as follows: (1) conduct a physical exam; (2) order magnetic resonance imaging ("MRI") to confirm the presence of a mass in the brain; (3) schedule a brain biopsy to obtain information about the tumor; (4) have a pathologist use the biopsy's histological information to determine the relevant diagnosis and treatment, e.g., the stage and location of the tumor; (5) analyze a tissue sample to determine the molecular subtype and genetic markers; and (6) prescribe effective treatment for the diagnosed GBM. The pathologist's report, and the results from the genetic analysis are vital to an oncologist's recommendation of radiation therapy and chemotherapy for patients.

The analysis of the tissue sample, usually a whole brain slide can take weeks, incurring costs and delaying potential treatment. The present invention solves this problem in the art, specifically for characterization of GBM, by integrating multiple biological feature classifiers into a single platform to generate relevant genetic, molecular, and histopathological information from a Whole Slide Image or WSI using a computer based classification analysis system. Results from exemplary embodiments can be received in seconds instead of weeks.

The popularity of high-resolution histopathological images over the past 10 years has encouraged the application of computational techniques to analyze tumors. In April 2017, the Food and Drug Administration (FDA) approved the sale of the first annotation system for WSIs, allowing pathologists to use a computer to view scanned slides as opposed to a microscope to manually examine slides.

By eliminating the need for high-throughput DNA methylation assays and whole-genome scans, exemplary embodiments save both time and money, both of which are valuable for a patient diagnosed with GBM. Additional embodiments may include a molecular test for subtype and linked molecular genetics for key genetic events including NF1 and PTEN loss, IDH1 and PI3K mutation, PDGFRA and EGFR amplification (i.e. genetic events that are best assayed on the DNA level) and MGMT methylation status".

Classification Systems

The invention relates to, among other things, characterizing glioblastomas based on histopathological data, preferably digital WSI.

As used herein, the classifications systems described may include computer executable software, firmware, hardware, or various combinations thereof. For example, the classification systems may include reference to a processor and supporting data storage. Further, the classification systems may be implemented across multiple devices or other components local or remote to one another. The classification systems may be implemented in a centralized system, or as a distributed system for additional scalability. Moreover, any reference to software may include non-transitory computer readable media that when executed on a computer, causes the computer to perform a series of steps, such as the methods according to exemplary embodiments.

The classification systems described herein may include data storage such as network accessible storage, local storage, remote storage, or a combination thereof. Data storage may utilize a redundant array of inexpensive disks ("RAID"), tape, disk, a storage area network ("SAN"), an internet small computer systems interface ("iSCSI") SAN, a Fibre Channel SAN, a common Internet File System ("CIFS"), network attached storage ("NAS"), a network file system ("NFS"), or other computer accessible storage. In one or more embodiments, data storage may be a database, such as an Oracle database, a Microsoft SQL Server database, a DB2 database, a MySQL database, a Sybase database, an object oriented database, a hierarchical database, or other database. Data storage may utilize flat file structures for storage of data. Exemplary embodiments used two Tesla K80 NVIDIA GPUs, each with 4992 CUDA cores and 11.2 GB of memory to train the deep learning algorithms. However, other systems may be used, and this exemplary hardware is meant to be illustrative and non-limiting.

In the first step, a classifier is used to describe a predetermined set of data. This is the "learning step" and is carried out on "training" data.

The training database is a computer-implemented store of data reflecting a plurality of histopathological data for a plurality of humans in association with a classification with respect to tumor characterization of each respective human. The format of the stored data may be as a flat file, database, table, or any other retrievable data storage format known in the art. In an exemplary embodiment, the test data is stored as a plurality of vectors, each vector corresponding to an individual human, each vector including a plurality of histopathological data measures for a plurality of histopathological data together with a classification with respect to tumor characterization of the human. Typically, each vector contains an entry for each histopathological data measure in the plurality of histopathological data measures. The training database may be linked to a network, such as the internet, such that its contents may be retrieved remotely by authorized entities (e.g., human users or computer programs). Alternately, the training database may be located in a network-isolated computer.

In the second step, which is optional, the classifier is applied in a "validation" database and various measures of accuracy, including sensitivity and specificity, are observed. In an exemplary embodiment, only a portion of the training database is used for the learning step, and the remaining portion of the training database is used as the validation database. In the third step, histopathological data measures from a subject are submitted to the classification system, which outputs a calculated classification (e.g., presence or absence of a tumor, characterization of a tumor) for the subject.

Several methods are known in the art for classification, including using classifiers such as support vector machines, AdaBoost, decisions trees, Bayesian classifiers, Bayesian belief networks, naïve Bayes classifiers, k-nearest neighbor classifiers, case-based reasoning, penalized logistic regression, neural nets, Random Forests, Fully Convolutional Networks (FCN), Convolutional Neural Networks, or any ensemble thereof. See e.g., Han & Kamber (2006) Chapter 6, *Data Mining, Concepts and Techniques,* 2nd Ed. Elsevier: Amsterdam. As described herein, any classifier or combination of classifiers (e.g., ensemble) may be used in a classification system.

Classifiers

There are many possible classifiers that could be used on the data. By way of non-limiting example, and as discussed herein, machine and deep learning classifiers such as support vector machines, genetic algorithms, penalized logistic regression, LASSO, ridge regression, naïve Bayes classifiers, classification trees, k-nearest neighbor classifiers, neural nets, elastic nets, Bayesian neural networks, Random Forests, gradient boosting trees, AdaBoost, Fully Convolutional Networks (FCN), Convolutional Neural Networks, or an ensemble thereof, may be used to classify the data. As discussed herein, the data may be used to train a classifier.

Machine learning is a subset of artificial intelligence that uses a machine's ability to take a set of data and learn about the information it is processing by changing the algorithm as data is being processed. Deep learning is a subset of machine learning that utilizes artificial neural networks inspired by the workings on the human brain. Exemplary embodiments lie in the field of computer vision, with overlaps with both of these fields. Computer Vision is a discipline that encompasses methods of acquiring, processing, analyzing, and understanding the content of digital images in the context of producing numerical or symbolic information. Accordingly, it should be appreciated that any specific architectures in these fields fall under exemplary technologies that may be used in combination.

Classification Trees

A classification tree is an easily interpretable classifier with built in feature selection. A classification tree recursively splits the data space in such a way so as to maximize the proportion of observations from one class in each subspace.

The process of recursively splitting the data space creates a binary tree with a condition that is tested at each vertex. A new observation is classified by following the branches of the tree until a leaf is reached. At each leaf, a probability is assigned to the observation that it belongs to a given class. The class with the highest probability is the one to which the new observation is classified.

Classification trees are essentially a decision tree whose attributes are framed in the language of statistics. They are highly flexible but very noisy (the variance of the error is large compared to other methods).

Tools for implementing classification trees as discussed herein are available, by way of non-limiting example, for the statistical software computing language and environment, R. For example, the R package "tree," version 1.0-28, includes tools for creating, processing and utilizing classification trees.

Random Forests

Classification trees are typically noisy. Random forests attempt to reduce this noise by taking the average of many trees. The result is a classifier whose error has reduced variance compared to a classification tree.

To grow a forest, the following algorithm is used:

1. For b=1 to B, where B is the number of trees to be grown in the forest,
   a. Draw a bootstrap sample[1].
   b. Grow a classification tree, $T_b$, on the bootstrap sample.

[1] A bootstrap sample is a sample drawn with replacement from the observed data with the same number of observations as the observed data.

2. Output the set $[T_b]^B_1$. This set is the random forest.

To classify a new observation using the random forest, classify the new observation using each classification tree in the random forest. The class to which the new observation is classified most often amongst the classification trees is the class to which the random forest classifies the new observation.

Random forests reduce many of the problems found in classification trees but at the price of interpretability.

Tools for implementing random forests as discussed herein are available, by way of non-limiting example, for the statistical software computing language and environment, R. For example, the R package "randomForest," version 4.6-2, includes tools for creating, processing and utilizing random forests.

AdaBoost (Adaptive Boosting)

AdaBoost provides a way to classify each of n subjects into two or more[2] disease categories based on one k-dimensional vector (called a k-tuple) of measurements per subject. AdaBoost takes a series of "weak" classifiers that have poor, though better than random, predictive performance[3] and combines them to create a superior classifier. The weak classifiers that AdaBoost uses are classification and regression trees (CARTs). CARTs recursively partition the dataspace into regions in which all new observations that lie within that region are assigned a certain category label. AdaBoost builds a series of CARTs based on weighted versions of the dataset whose weights depend on the performance of the classifier at the previous iteration. Han & Kamber (2006) *Data Mining, Concepts and Techniques*, 2nd Ed. Elsevier: Amsterdam.

[2] AdaBoost technically works only when there are two categories to which the observation can belong. For g>2 categories, (g/2) models must be created that classify observations as belonging to a group of not. The results from these models can then be combined to predict the group membership of the particular observation.

[3] Predictive performance in this context is defined as the proportion of observations misclassified.

Convolutional Neural Network

Convolutional Neural Network (CNN or ConvNet) is a class of deep, feed-forward artificial neural networks, most commonly applied to analyzing visual imagery. CNNs use a variation of multilayer perceptrons designed to require minimal preprocessing. They are also known as shift invariant or space invariant artificial neural networks (SIANN), based on their shared-weights architecture and translation invariance characteristics. Convolutional networks were inspired by biological processes in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field. CNNs use relatively little pre-processing compared to other image classification algorithms. This means that the network learns the filters that in traditional algorithms were hand-engineered. This independence from prior knowledge and human effort in feature design is a major advantage. LeCun and Bengio (1995) "Convolutional networks for images, speech, and time-series," in M. A. Arbib, editor, *The Handbook of Brain Theory and Neural Networks*, MIT Press. Fully convolutional indicates that the neural network is composed of convolutional layers without any fully-connected layers or MLP usually found at the end of the network.

Methods of Classifying Data Using Classification System(s)

The invention provides for methods of classifying data (test data, i.e., histopathological data and genetic information) obtained from an individual. These methods involve preparing or obtaining training data, as well as evaluating test data obtained from an individual (as compared to the training data), using one of the classification systems including at least one classifier as described above. Preferred classification systems use classifiers such as, but not limited to, support vector machines (SVM), AdaBoost, penalized logistic regression, naïve Bayes classifiers, classification trees, k-nearest neighbor classifiers, neural nets, random forests, Fully Convolutional Networks (FCN), Convolutional Neural Networks (CNN), and/or a combination thereof. The classification system outputs a classification of the individual based on the test data.

Particularly preferred for the present invention is an ensemble method used on a classification system, which combines multiple classifiers. For example, an ensemble method may include SVM, AdaBoost, penalized logistic regression, naïve Bayes classifiers, classification trees, k-nearest neighbor classifiers, neural nets, Fully Convolutional Networks (FCN), Convolutional Neural Networks (CNN), Random Forests, or any ensemble thereof, in order to make a prediction regarding tumor pathology (e.g., glioblastoma molecular subtype classification, MGMT methylation status, tumor features). The ensemble method was developed to take advantage of the benefits provided by each of the classifiers, and replicate measurements of each WSI specimen.

The histopathological data measures for each of the histopathological data items in each subject's biopsy sample are obtained. Typically, a physical exam is conducted, an MRI is used to confirm the presence of a mass in the brain, and a brain biopsy is performed, and a whole brain slide is prepared with image data collected, genetic information is collected (e.g., MGMT methylation), a full complement of histopathological data measures are obtained for each sample. Each subject may be predicted as having tumor (e.g., as glioblastoma or normal) based on each of the replicate measurements (e.g., duplicate, triplicate) using a classification system including at least one classifier, yielding multiple predictions (e.g., four predictions, six predictions). In the preferred mode of this invention, the ensemble methodology may predict the subject to have a glioblastoma if at least one of the predictions was glioblastoma and all of the other predictions predict the subject to be normal. The decision to predict a subject as having glioblastoma if only one of the predictions from the classifier(s) is positive for glioblastoma was made in order for the ensemble methodology to be as conservative as possible. In other words, this test was designed to err on the side of identifying a subject as having glioblastoma in order to minimize the number of false negatives, which are more serious errors than false positive errors. The ensemble methodology may predict that the subject has, for example, glioblastoma if at least two, or at least three, or at least four, or at least five, up to all of the predictions, are positive for glioblastoma.

The test data may be any histopathological data, such as brain biopsy image, for example digital whole-slide hematoxylin and eosin (H&E) stained histopathology WSI. However, data from other imaging techniques, such as, but not limited to, Magnetic Resonance Images (MRIs), Proton Emission Tomography (PET) scans, Computer Tomography (CT) scans, and X-Ray images may be used.

In one embodiment, the invention provides a method of classifying test data, the test data comprising histopathological data comprising: (a) accessing an electronically stored set of training data vectors, each training data vector or k-tuple representing an individual human and comprising histopathological data for the respective human for each replicate, the training data vector further comprising a classification with respect to tumor characterization of each respective human; (b) training an electronic representation of a classifier or an ensemble of classifiers as described herein using the electronically stored set of training data vectors; (c) receiving test data comprising a plurality of histopathological data for a human test subject; (d) evaluating the test data using the electronic representation of the classifier and/or an ensemble of classifiers as described herein; and (e) outputting a classification of the human test subject based on the evaluating step.

In another embodiment, the invention provides a method of classifying test data, the test data comprising histopathological data comprising: (a) accessing an electronically stored set of training data vectors, each training data vector or k-tuple representing an individual human and comprising histopathological data for the respective human for each replicate, the training data further comprising a classification with respect to tumor characterization of each respective human; (b) using the electronically stored set of training data vectors to build a classifier and/or ensemble of classifiers; (c) receiving test data comprising a plurality of Whole Slide Images (WSI) for a human test subject; (d) evaluating the test data using the classifier(s); and (e) outputting a classification of the human test subject based on the evaluating step. Alternatively, all (or any combination of) the replicates may be averaged to produce a single value for each histopathological data for each subject. Outputting in accordance with this invention includes displaying information regarding the classification of the human test subject in an electronic display in human-readable form.

The classification with respect to tumor characterization may be the presence or absence of a brain tumor such as glioblastoma. For example, providing a characterization of the glioblastoma comprising tumor features, tumor molecular subtype classification, and MGMT promoter methylation classification. The characterization may comprise identification of the tumor as a glioblastoma, preferably comprising molecular subtype classification as a Classical, Mesenchymal, Proneural, or Neural glioblastoma. The characterization may comprise identification of the tumor as a glioblastoma and that the glioblastoma is either MGMT+ or MGMT−. The characterization may comprise identification of the tumor as a glioblastoma and histopathological data comprising leading edge (LE), infiltrating tumor (IT), cellular tumor (CT), perinectronic zone (CTpnz), necrosis (CTne), pseudopalisading cells (CTpan), hyperplastic blood vessels (hbv), or a combination thereof.

The set of training vectors may comprise at least 20, 25, 30, 35, 50, 75, 100, 125, 150, or more vectors.

It were understood that the methods of classifying data may be used in any of the methods described herein. In particular, the methods of classifying data described herein may be used in methods for tumor characterization, based in part on a classification according to this invention, and methods of confirming that a brain tumor is a GBM.

Classifying Data Using Reduced Numbers of Histopathological Data

The disclosure provides for a computer implemented method for characterization of a tumor comprising: receiving, on at least one processor, histopathological data from a subject, for example, digital whole slide image from a brain biopsy; evaluating, using the at least one processor, the data using a classifier which is an electronic representation of a classification system, each said classifier trained using an electronically stored set of training data vectors, each training data vector representing an individual human and data for the respective human, each training data vector further comprising a classification with respect to the characterization of the brain tumor in the respective human; and outputting, using the at least one processor, a classification of the sample from the human test subject concerning the characterization of the brain tumor in the subject based on the evaluating step. This is a problem in the field precision medicine pipeline which is determining the characteristics of a tumor that can be used for personalized treatment. The methods and systems described herein provide a solution specifically addresses this problem for tumors, for example, GBMs.

Classification system suitable for use in the methods described herein may be selected from the group consisting of support vector machines, genetic algorithms, penalized logistic regression, LASSO, ridge regression, naïve Bayes classifiers, classification trees, k-nearest neighbor classifiers, neural nets, elastic nets, Bayesian neural networks, Random Forests, gradient boosting trees, AdaBoost, Fully Convolutional Networks (FCN), Convolutional Neural Networks (CNN), or an ensemble thereof, may be used to classify the data. As discussed herein, the data may be used to train a classifier.

In the methods described herein, the test data and each training data vector may further comprises at least one additional characteristic selected from the group consisting of the sex, age, genetic information, biomarkers, and smoking status of the individual human.

The data may comprise histopathological data, genetic information, or a combination thereof. For example, the histopathological data may be obtained from a whole brain slide. The histopathological data comprises leading edge (LE), infiltrating tumor (IT), cellular tumor (CT), perinectronic zone (CTpnz), necrosis (CTne), pseudopalisading cells (CTpan), hyperplastic blood vessels (hbv), or a combination thereof.

Genetic information comprises changes in EGFR, NF1, PDGFRA/IDH1, and neuronal genes, preferably mutations, including but not limited to chromosome 7 amplification, chromosome 10 deletion, high-level EGFR amplification, deletions in NF1 gen, high expression of CH13L1 gene, high expression of MET gene, alternations of PDFRA gene, point mutations in IDH1, TP53 mutation, expression of neuron markers by astrocytes, O6-methylguanine-DNA methyltransferase (MGMT) methylation, or a combination thereof. The neuron markers comprise NEFL, GABA Receptor α1, SYT1, SLC12A5.

The characterization may comprise identification of the tumor as a glioblastoma, preferably comprising molecular subtype classification as a Classical, Mesenchymal, Proneural, or Neural glioblastoma. The characterization may comprise identification of the tumor as a glioblastoma and that the glioblastoma is either MGMT+ or MGMT−.

The characterization may comprise tumor features, MGMT methylation, molecular subtype determination, and combinations thereof.

Patients with glioblastoma, the most aggressive type of brain cancer, have an average survival of less than one year post-diagnosis. Thus, it is critical to determine the most effective patient-specific treatment quickly. Obtaining accurate tumor information in a timely manner greatly increases the specificity of targeted treatment by an oncologist. Exemplary embodiments, which may be referred to as GlioVision, generate the following information about a glioblastoma tumor from a brain biopsy slide using neural networks: annotated areas of relevant tissues, molecular subtype, and expression status of an important gene. Exemplary embodiments have achieved 86%, 94%, and 96% accuracy in these three tasks, respectively. In contrast, current methods take over one week to gather this information from expensive gene tests, while the data-driven approach of the exemplary embodiments takes less than five seconds for a fraction of the cost.

The system and methods described herein may be used to provide personalized, targeted treatment for patients with cancer. Exemplary embodiments identify a significant disconnect in the treatment of patients in the current medical system. Specifically, society has made leaps and bounds towards creating therapies targeted for a cancer's specific genetic mutations, but has not significantly sped up the process for obtaining this tumor information. This seeming disconnect is likely the reason that in the past thirty years, the mortality rate for patients with glioblastoma has not decreased (and this trend follows the same for many types of aggressive cancers). The result of the system and methods described herein makes the adoption of precision medicine techniques economical for every hospital in the country. Exemplary embodiments described herein can determine relevant characteristics of a tumor in a fraction of the time and cost of traditional methods by using a scanned image of a biopsy rather than a DNA sample. Traditional methods are a whole genome sequencing for mutations, methylation arrays/RNA expression data for gene expression. The main differentiator: the process of predicting molecular and genetic information about a tumor from a scanned biopsy slide (using artificial intelligence (AI), specifically deep learning and computer vision).

The system and methods described herein can determine relevant characteristics of a tumor in a fraction of the time and cost of traditional methods by using a scanned image of a biopsy rather than a DNA sample. Traditional methods is whole genome sequencing for mutations, methylation arrays/RNA expression data for gene expression.

A differentiator between prior methods and the system and methods described herein is that this process of predicting molecular and genetic information about a tumor from a scanned biopsy slide, for example, a WSI, using artificial intelligence or AI, specifically deep learning and computer vision.

Exemplary embodiments provide for methods of classifying data (such as test data obtained from an individual) that involve histopathological data. That is, training data may be thinned to exclude all but a subset of histopathological data for a selected subset of histopathological data. Likewise, test data may be restricted to a subset of histopathological data from the same histopathological data.

In one embodiment, exemplary embodiments provide a method of classifying test data, the test data comprising histopathological data measures that are a plurality of histopathological data measures of each of a set of histopathological data comprising: (a) accessing an electronically stored set of training data vectors, each training data vector representing an individual human and comprising histopathological data for the respective human, each training data vector further comprising a classification with respect to tumor characterization of the respective human; (b) selecting a subset of histopathological data from the set of histopathological data; (c) training an electronic representation of a learning machine, such as a classifier or an ensemble of classifiers as described herein, using the data from the subset of histopathological data of the electronically stored set of training data vectors; (d) receiving test data comprising a plurality of histopathological data for a human test subject related to the set of histopathological data in step (a); (e) evaluating the test data using the electronic representation of the learning machine; and (f) outputting a classification of the human test subject based on the evaluating step.

It is within the contemplation of this disclosure to contemporaneously determine histopathological data measures of additional histopathological data whether or not associated with the tumor of interest. Determination of these additional histopathological data measures will not prevent the classification of a subject according to the present invention. However, the maximum number of histopathological data whose measures are included in the training data and test data of any of the methods of this invention. A skilled person would understand that the number of histopathological data should be limited to avoid inaccurate predictions due to overfitting. The subsets of histopathological data may be determined by using the methods of reduction described herein. A reduced model of particular subsets of histopathological data are described herein.

According to exemplary embodiments, the histopathological data are chosen from a computed subset which contains the histopathological data contributing a highest measure of model fit. As long as those histopathological data are included, exemplary embodiments do not preclude the inclusion of a few additional histopathological data that do not necessarily contribute. Nor will including such additional histopathological data measures in a classifying model preclude classification of test data, so long as the model is devised as described herein.

In another mode, the selected histopathological data are chosen from a computed subset from which histopathological data that contribute the least to a measure of model fit have been removed. As long as those selected histopathological data are included, the invention does not preclude the inclusion of a few additional histopathological data that do not necessarily contribute. Nor will including such additional histopathological data measures in a classifying model preclude classification of test data, so long as the model is devised as described herein. In other embodiments, histopathological data are determined for the subject, and the same number of whole brain slide image data are used in the training phase.

It were understood that the methods of classifying data from the histopathological data may be used in any of the methods described herein. In particular, the methods of classifying data using histopathological data described herein may be used in methods for tumor characterization, based in part on a classification according to this invention, and methods of diagnosing brain tumors, including glioblastomas. Other histopathological data, other than a WSI may also be added. These additional histopathological data may or may not contribute to or enhance the characterization of the tumor or diagnosis.

Specifically, the disclosure relates to a platform that uses trained machine learning architecture, for example, neural networks, and datasets of WSIs to extract relevant histopathological and genetic information to enable an oncologist and other professionals within the field to prescribe aggressive treatments with confidence in a timely manner. The disclosure relies on a tile-based image analysis approach. The tiles of interest are segmented as inputs, and the input WSIs are preprocessed using techniques such as tiling and cyclic pooling and trained with networks initialized via a transfer learning technique.

Exemplary embodiments provide an assessment platform that uses state-of-the-art neural networks and a dataset of over 150 WSIs to extract relevant histopathological and genetic information. The input WSIs were preprocessed using techniques such as tiling and cyclic pooling and trained with networks initialized via the transfer learning technique. The networks exhibited 86%, 94%, and 96% testing accuracy for feature segmentation, subtype classification, and MGMT methylation prediction, respectively. Exemplary embodiments provide a high speed (e.g., 5 seconds), low cost, and ready to implement with significantly improved accuracy.

Exemplary embodiments include methods and systems using three network models: one for tumor feature segmentation; one for tumor molecular subtype; and one for MGMT promoter methylation status. These networks are trained with a combination of two separate datasets.

The two datasets include digital whole slide hematoxylin and eosin ("H&E") stained histopathology WSI. The WSIs are high-magnification digital images of a single microscope slide, plated with brain tissue from a biopsy. The combination of hematoxylin; nuclear feature-defining stain; and eosin, a counterbalance color; is the primary technique in the histopathological laboratory. The WSIs for both datasets were saved in the .sys format consisting of .tiff images saved at multiple resolution levels, as shown in FIG. 1. Exemplary image 100 in FIG. 1 shows three different magnification levels (110, 120, 130). These magnification levels are exemplary and meant to be non-limiting. According to exemplary embodiments, the WSIs were previously annotated by a pathologist or other professional indicating the necrosis and tissue regions in the slide image, saved in an .xml format. The combination of two datasets was chosen in order to maximize slide variability in order to best represent clinical samples from a variety of sources.

Figure 2B:
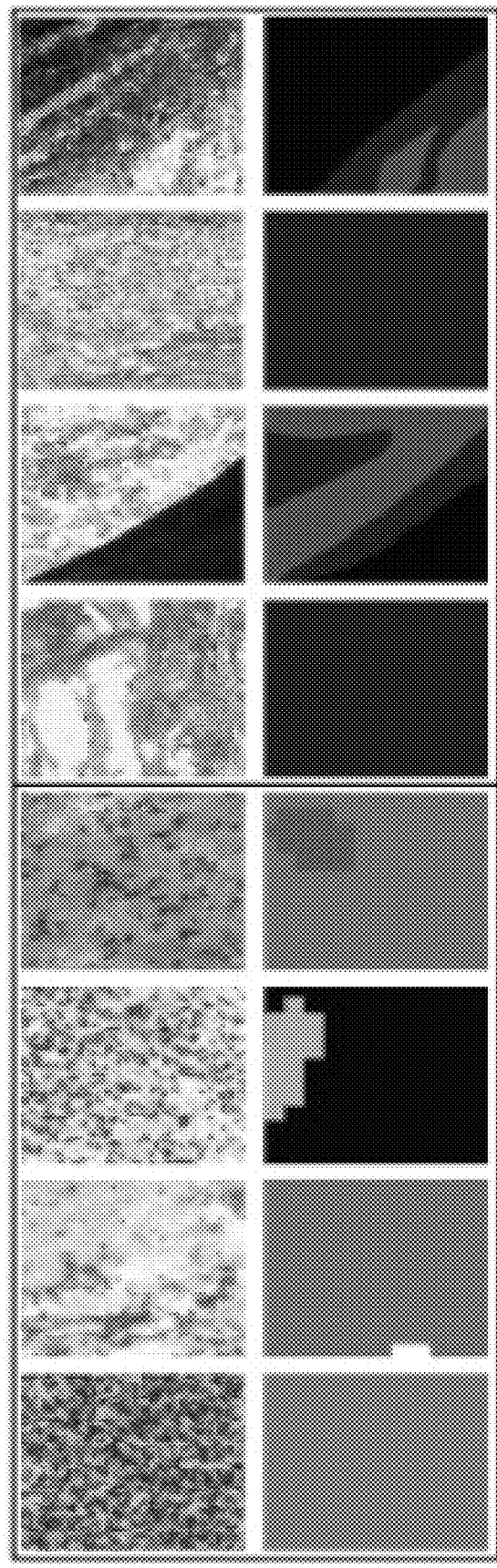
FIG. 2B depicts an example of eight tissue samples at 40× magnification from the IVYGAP (left 4) and The Cancer Genome Atlas ("TCGA") (right 4) datasets with associated ground truth mask tile.

Examples of datasets include WSIs from TCGA database maintained by the National Institute of Health, and the IVYGAP maintained by the Allen Institute for Brain Science. The respective datasets are annotated. FIGS. 2A and 2B includes the annotated descriptions of the datasets.

The first dataset included 143 publicly available WSIs obtained from The Cancer Genome Atlas (TCGA) database maintained by the National Institutes of Health (NIH). The database includes two types of brain cancer: glioblastoma multiforme (GBM) and lower grade glioma (LGG). Only the 50 GBM images were selected for this study in order to standardize the tumor grading. This dataset was obtained with pathologist annotations from Emory University, which indicate cellular tumor (blue), necrosis (red), and background areas (black). The TCGA dataset was chosen for its extensive government and private industry contributions, research institute support, open-source nature, and large number of samples.

The second dataset was the IVY Glioblastoma Atlas Project (IVYGAP) maintained by the Allen Institute for Brain Science. This dataset contains over 300 WSIs with associated annotated images indicating tumor regions such as leading edge (LE), infiltrating tumor (IT), cellular tumor (CT), perinectronic zone (CTpnz), necrosis (CTne), pseudopalisading cells (CTpan), and hyperplastic blood vessels (hbv) defined by the Allen Institute with definitions in FIG. 2A at table 200. The IVYGAP dataset was chosen for this task because of the accuracy of the annotations, which were a result of agreement from multiple neuropathologists.

Because they were gathered from several different sources, the datasets had WSIs that varied in resolution, quality, and color, as shown in FIG. 2B at 250. While this variation can pose a more challenging segmentation problem than using a uniform dataset, it may actually be beneficial for training the classifiers, as it makes the overall system more robust and better suited for real-world applications where significant variation can occur.

While the automatic segmentation of the image detailed in exemplary embodiments includes many tissues that are biologically defined and taken into consideration in the normal workflow of a pathologist, other tissues are arbitrarily defined and outside of the scope of a pathologist. Therefore, the choices of tissues chosen in the workflow described herein are defined specifically for this application. For a different disease, slightly modified tissues would be segmented. Thus, exemplary embodiments could be modified to work with different diseases.

Overall System and Data Flow

Exemplary embodiments may use Caffe. Caffe is a deep learning framework developed by Berkeley Artificial Intelligence Research with expression, speed, and modularity in mind. Caffe was chosen, in part, because of its adaptable code structure, high speed, and extensive community support. Additionally, the embodiment utilizes an artificial neural network. Artificial Neural Networks have proven successful in complex computer vision tasks, as they extract complex patterns and trends not visible to humans or other computer algorithms. Further, the embodiment uses Python Imaging Library ("PIL") to perform image processing. Python used because of its interaction with Caffe, and standard machine learning and numerical libraries. The Python script is hosted by a cloud server.

A processing unit, including memory comprising computer-readable instructions, is used to train deep learning algorithms. Exemplary embodiments used two Tesla K80 NVIDIA Graphic Processing Unit ("GPU"), each with 4992 Compute Unified Device Architecture cores and 11.2 GB of memory. This example is meant to be non-limiting as other computer hardware could be used.

Figure 3:
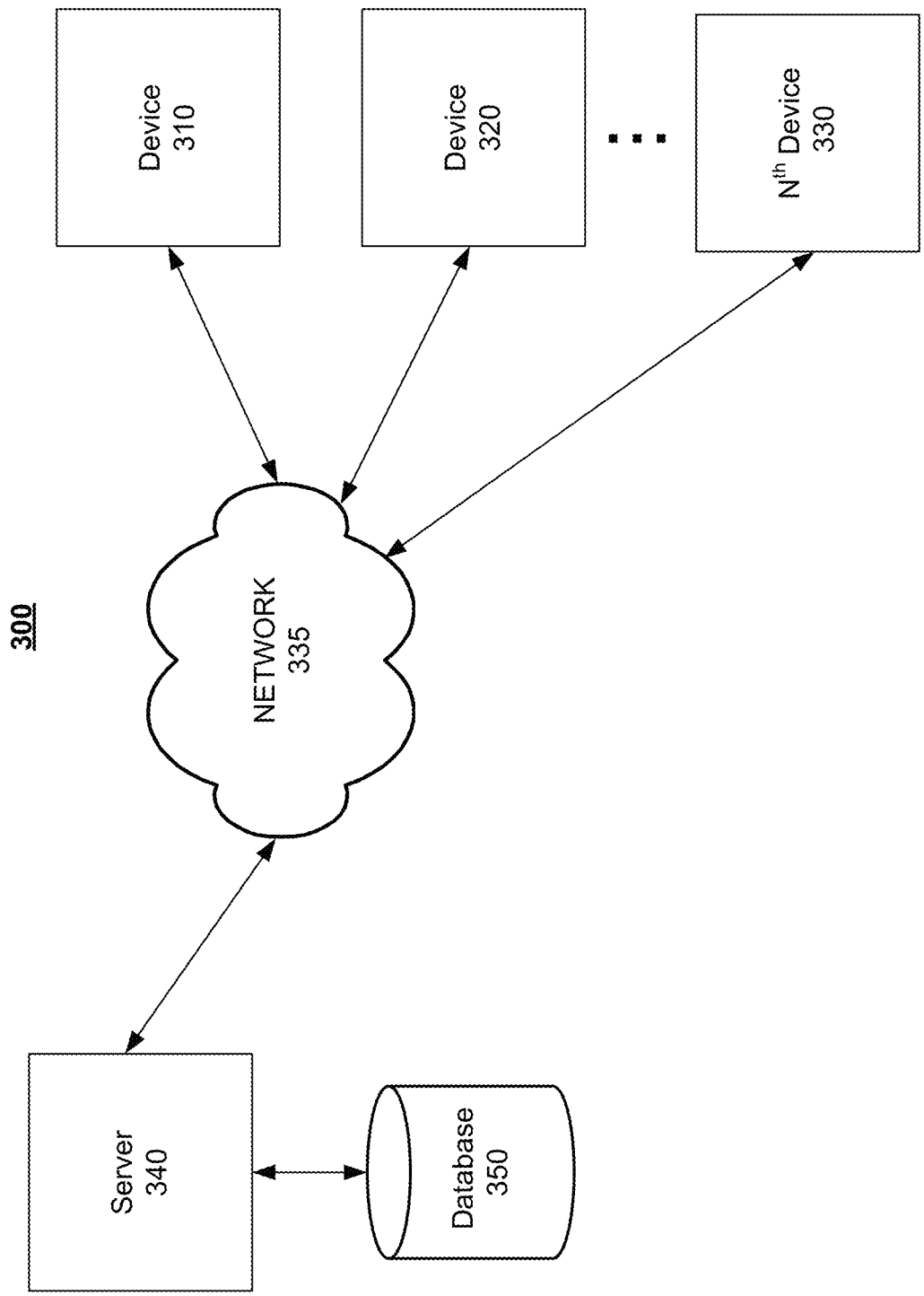
FIG. 3 depicts a system according to an exemplary embodiment.

FIG. 3 represents an exemplary system 300. The system 300 may have one or more devices (310, 320, 330), a network (335), a server (340), and a database (350). The one or more devices (310, 320, 330) that serve as an interface point to an application as described in FIGS. 4A and 4B. For example, the interface may be with a web application (i.e., GlioVision) as described herein. The devices (310, 320, 330) may each be a processing machine. Each device may provide processing, display, storage, communications, and execution of commands in response to inputs from a user thereof and respond to requests from installed software and/or modules.

The devices (310, 320, 330) may each serve as a client side. The devices may be configured to perform other functions and processing beyond the methods described herein. For example, the devices may be multi-functional in operation. The devices may each support the operation and running of one or more applications or programs. For example, devices (310, 320, 330) may include one or more computer processors and be capable of being programmed to execute certain tasks. According to exemplary embodiments, the devices (310, 320, 330) may be types of computing platforms, such as, for example, a desktop computer or a laptop computer. The devices (310, 320, 330) may be a combination of computing devices, such as a combination of portable electronic devices and other computing platforms. According to some embodiments, the devices (310, 320, 330) may be portable electronic devices or mobile electronic devices. A user may interact with the portable electronic device through various input devices (not shown). The portable electronic devices may have communication capabilities over both cellular and wireless type networks to transmit/receive data and/or voice communications.

For example, portable electronic devices, by way of non-limiting examples, may include such portable computing and communications devices as mobile phones (e.g., cell or cellular phones), smart phones (e.g., iPhones, Android based phones, or Blackberry devices), personal digital assistants (PDAs) (e.g., Palm devices), laptops, netbooks, tablets, or other portable computing devices. These portable electronic devices may communicate and/or transmit/receive data over a wireless signal. The wireless signal may consist of Bluetooth, Wireless Application Protocol (WAP), Multimedia Messaging Service (MMS), Enhanced Messaging Service (EMS), Short Message Service (SMS), Global System for Mobile Communications (GSM) based systems, Code Division Multiple Access (CDMA) based systems, Transmission Control Protocol/Internet (TCP/IP) Protocols, or other protocols and/or systems suitable for transmitting and receiving data from the portable electronic device. The portable electronic device may use standard wireless protocols which may include IEEE 802.11a, 802.11b, 802.11g, and 802.11n.

The devices (310, 320, 330) may be communicatively coupled to a network (335). In various embodiments, the network (335) may be more than one network. The devices (310, 320, 330) may establish communications with other parts the system 300, such as server (340), over the network (335). Upon successful initiation of communications between the devices (310, 320, 330) and the network (335) and another part of the system 300, such as, for example, server (340), data may be exchanged between device (310, 320, 330) and the server (340) over the network (335). Data may be transmitted to/from the devices (310, 320, 330) to/from the server (340). The devices (310, 320, 330) may be geographically dispersed from each other and the server (940).

The network (335) may be a computer based network, with one or more servers and/or computer processors. For example, the network (335) may be the Internet or a network connected to the Internet. The network (335) may be a satellite or cellular based network. Information and data may be exchanged through the network (335) between the various components of the system 300. In various embodiments, the network (335) may be a local area network that may be connected to and/or interfaces with the Internet. It should be appreciated that the network may be a combination of local area networks, wide area networks, and external networks, which may be connected to the Internet.

The server (340) may contain the code which is executed to process the uploaded WSI and provide the output information. The server (340) may be more than one server. The output information may then be displayed on the devices (310, 320, 330). The server (340) may be communicatively coupled with a database (350). The database (350) may be more than one database.

The server (340) may be communicatively coupled to the network (335). The server (340) may perform operations associated with the establishment, configuration, and application of the application described herein accordingly to exemplary embodiments.

The server (340) may have a database (350) communicatively coupled thereto. The database (350) may contain data and information used by the system 300. For example, the database may store information as described herein used by exemplary embodiments relating to GBM and tumors. Additional information may be contained therein related to the operation and administration of the system 300.

The database (350) may include any suitable data structure to maintain the information and allow access and retrieval of the information. For example, the database may keep the data in an organized fashion. The database (350) may be a database, such as an Oracle database, a Microsoft SQL Server database, a DB2 database, a MySQL database, a Sybase database, an object oriented database, a hierarchical database, a flat database, and/or another type of database as may be known in the art that may be used to store and organize rule data as described herein.

The database (350) may be stored in any suitable storage device. The storage device may include multiple data storage devices. The multiple data storage devices may be operatively associated with the database (350). The storage may be local, remote, or a combination thereof with respect to the database. The database (350) may utilize a redundant array of disks (RAID), striped disks, hot spare disks, tape, disk, or other computer accessible storage. In one or more embodiments, the storage may be a storage area network (SAN), an internet small computer systems interface (iSCSI) SAN, a Fiber Channel SAN, a common Internet File System (CIFS), network attached storage (NAS), or a network file system (NFS). The database may have back-up capability built-in. Communications with the database (350) may be over a network, such as the network (335), or communications may be over a direct connection between the database (350) and the server (340), as depicted in FIG. 3. Data may be transmitted and/or received from the database (350). Data transmission and receipt may utilize cabled network or telecom connections such as an Ethernet RJ15/Category 5 Ethernet connection, a fiber connection, a traditional phone wireline connection, a cable connection or other wired network connection. A wireless network may be used for the transmission and receipt of data.

Figure 4B:
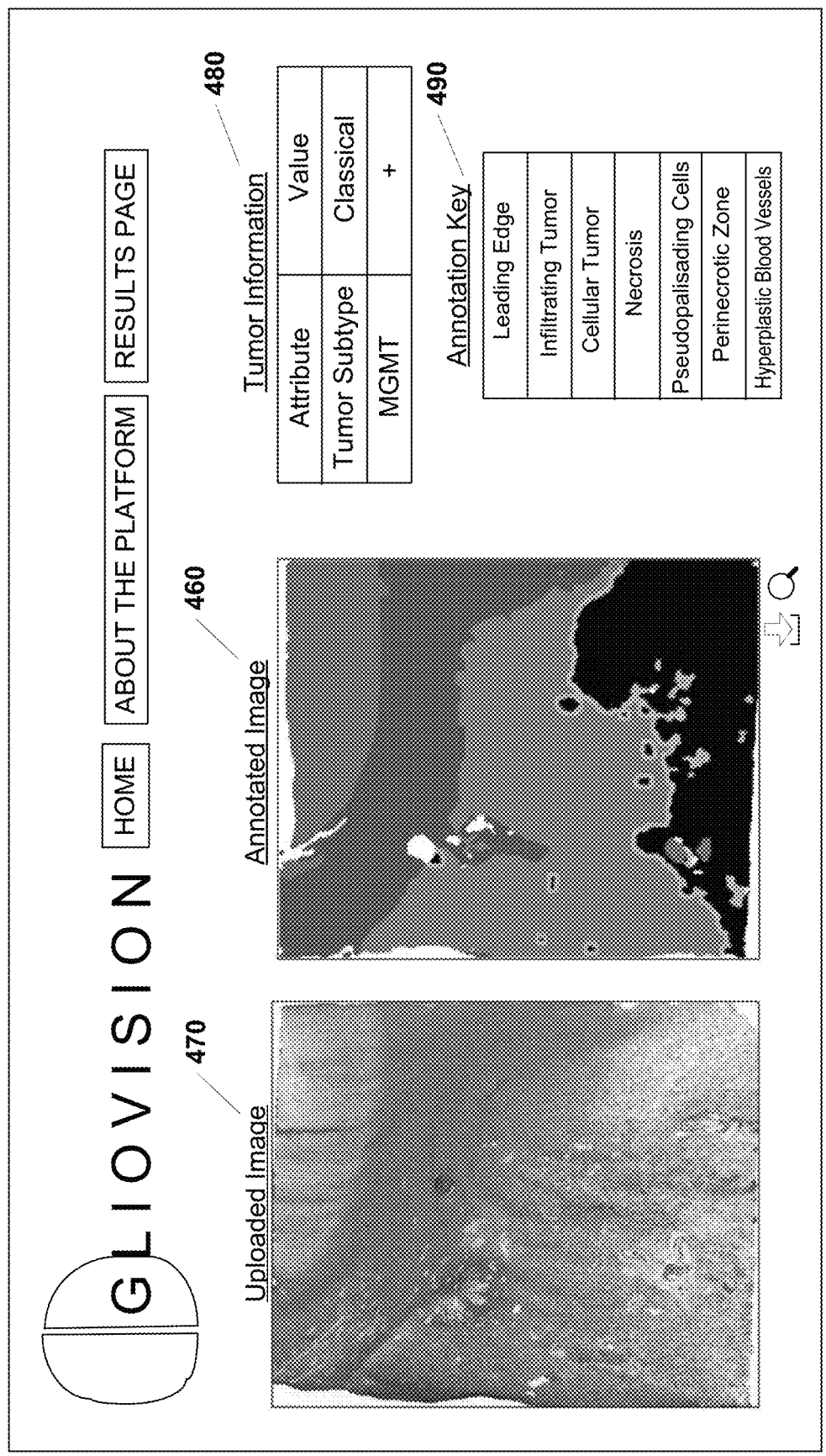
FIG. 4B depicts a results page of the web application according to an exemplary embodiment.

FIGS. 4A and 4B depict screenshots of an exemplary web application (400, 450) according to exemplary embodiments web application. The web application may be accessed by the one or more devices of the system 100. The web application may be hosted by the server(s) of the system 100. According to exemplary embodiments, the web application may be referred to as "GlioVision." However, this embodiment is meant to be non-limiting.

According to exemplary embodiments, the website includes information about glioblsatoma, the deep learning algorithms employed, and the information displayed following the analysis of the WSI. The web application was developed to give a pathologist or oncologist the means to easily utilize the technology in their clinical environment. The user inputs a scanned WSI, as shown at 410 in FIG. 4A, which is then sent to a cloud server hosting a Python script encompassing the preprocessing steps as well as an implementation of the trained neural networks. The output is an annotated image consisting of the patches outputted by the network, the subtype of the tumor, and the MGMT promoter methylation status, as shown in FIG. 4B at 460, which can be compared to the uploaded image 470. Tumor information (480) and an annotation key (490) are also provided in FIG. 4B.

Figure 5:
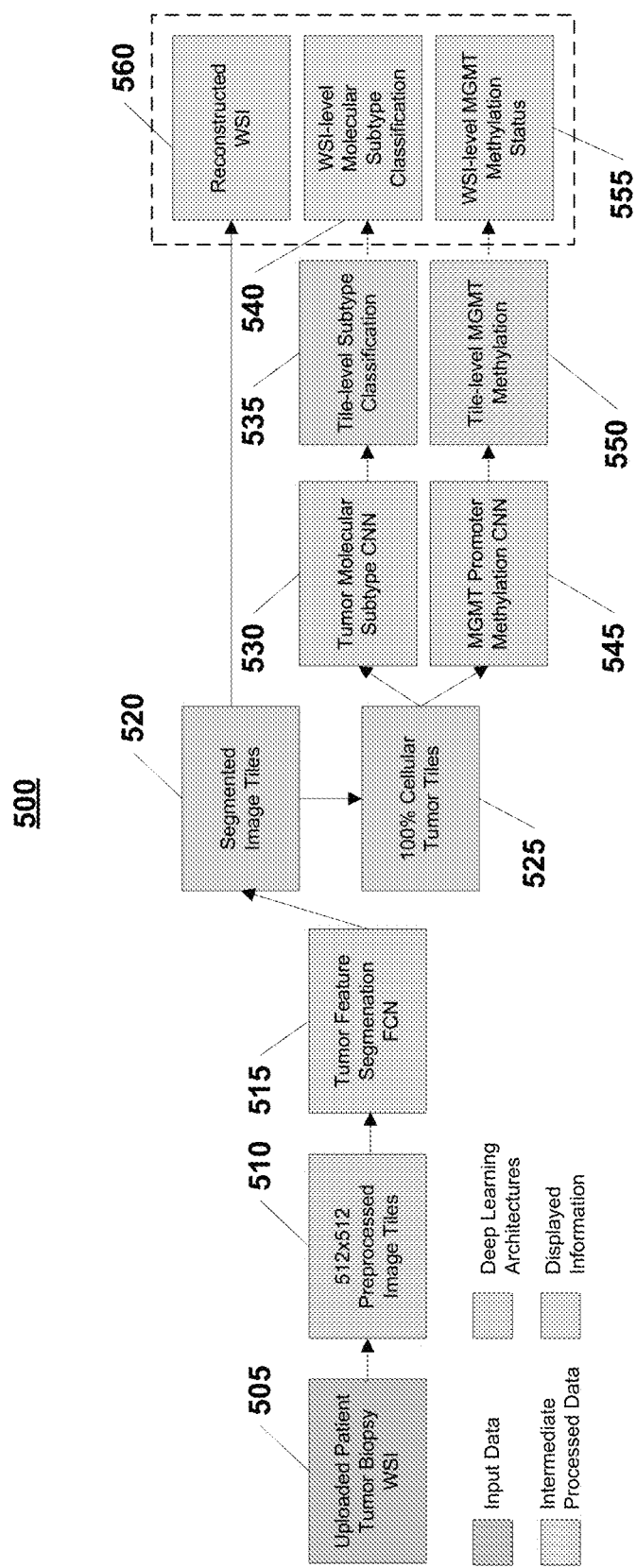
FIG. 5 depicts an overall data flow according to an exemplary embodiment.

The objective of exemplary embodiments was to develop a completely data-driven approach integrating multiple biological feature classifiers into a single platform for the generation of relevant genetic, molecular, and histopathological information from a WSI. Computationally segmenting relevant histopathological information from a brain biopsy offers second opinions for pathologists in a time-efficient manner and a concrete, data-driven approach to diagnosis for patients. From the molecular subtype and MGMT methylation results, an oncologist can prescribe personalized chemotherapy and radiation therapy that will be most effective for the patient. FIG. 5 at 500 depicts an overall data flow according to exemplary embodiments. The data may begin at block 505 with an upload of a patient tumor biopsy WSI. At block 510, the WSI is preprocessed into image tiles (512×512). At block 515, the tumor features are segmented. At block 520, segmented image tiles are created. At block 525, tumor cellular tiles are extracted. At block 530, a tumor molecular subtype CNN is used. At block 535, a tile-level subtype classification is made. At block 540, a WSI-level molecular subtype classification is output. At block 545, a MGMT promotor methylation CNN is used. At block 550, a tile-level MGMT methylation is made. At block

555, a WSI-level MGMT methylation status is output. At block 560, a reconstructed WSI is output.

In the data flow 500, block 505 represents input data; blocks 510, 520, 525, 535, and 550 represent intermediate processed data; blocks 515, 530, and 545 represent deep learning architectures; and blocks 560, 540, and 555 represent displayed information.

Preprocessing: Tissue Tile Extraction and Data Augmentation

Figure 6:
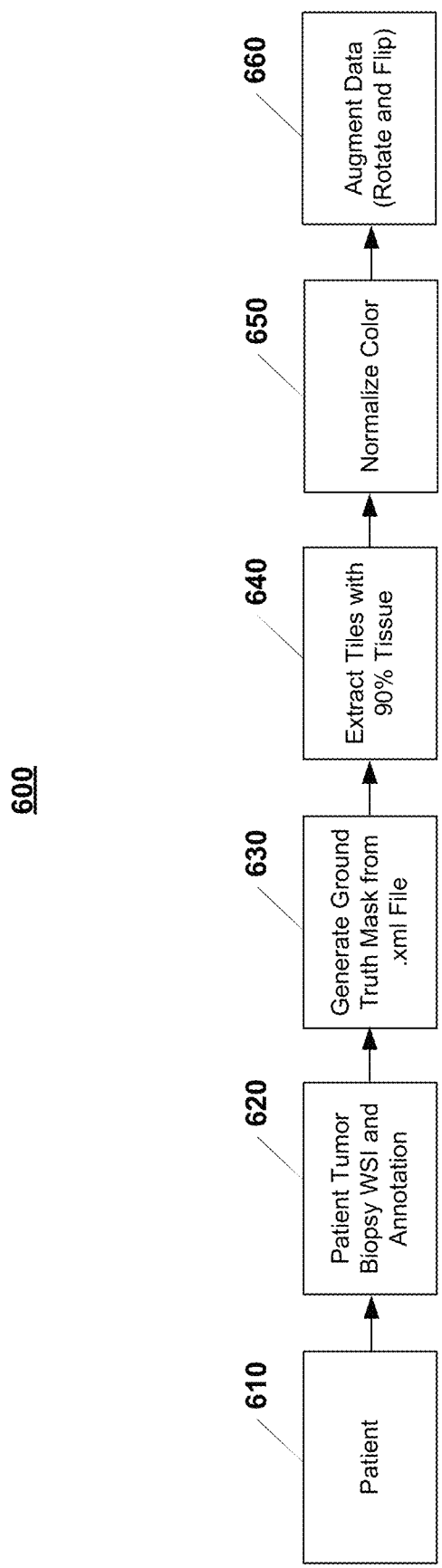
FIG. 6 depicts a flowchart of the pre-processing methods according to an exemplary embodiment.
Figure 7:
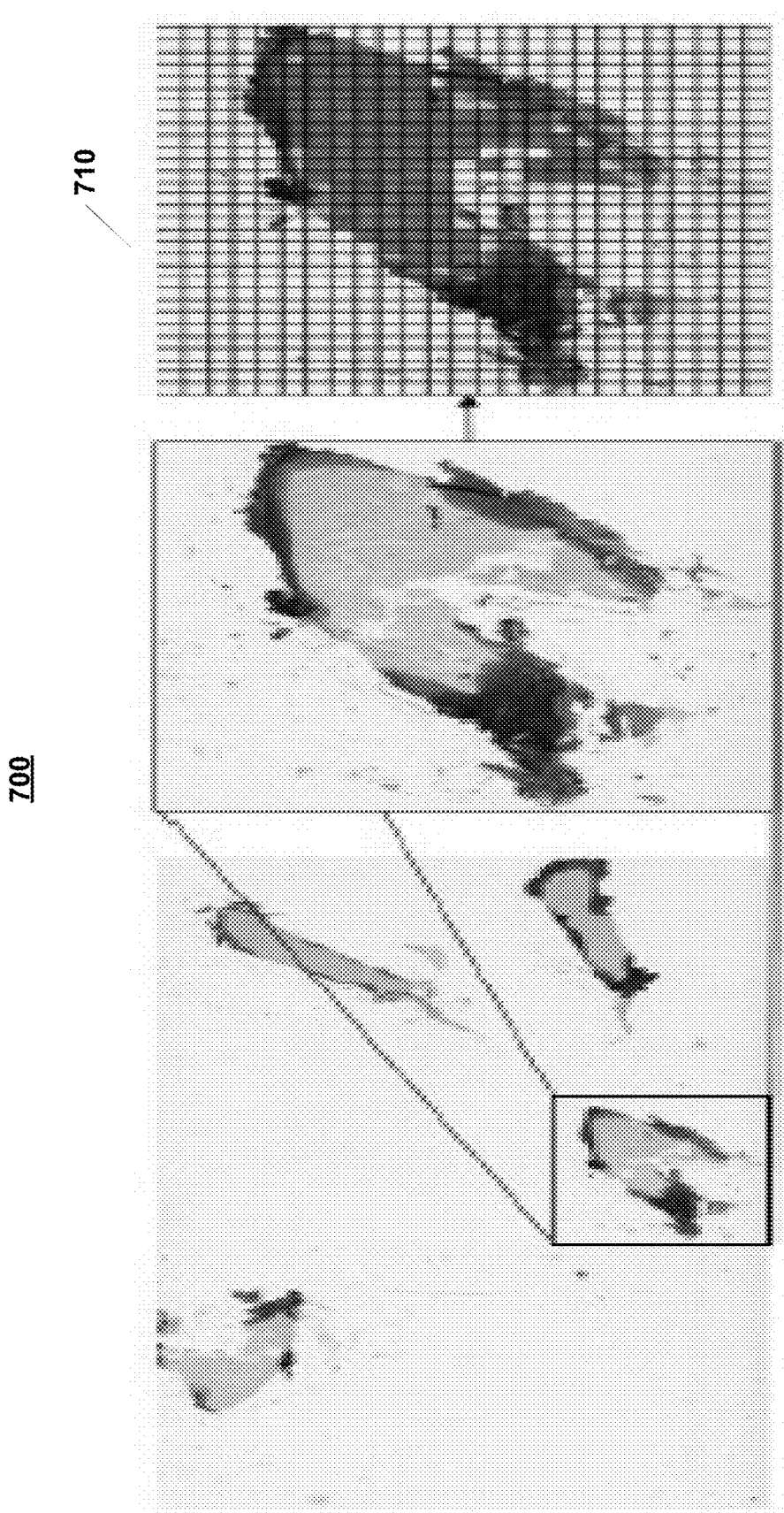
FIG. 7 depicts an example of the tissue segmentation algorithm on a sample WSI from the TCGA database, wherein the tiles with over 90% tissue regions are darkened.

A tile-based image analysis framework is an exemplary method implemented for tissue extraction and data augmentation, as shown in FIG. 6 at 600, wherein the WSI and a ground truth mask are divided into a lattice of square tiles, and tiles of interest are segmented into output, as shown in FIG. 7 at 700. In 700, at image 710, tiles with over 90% tissue regions are darkend.

The method 600 begins at block 610 with a patient. At block 620, a patient tumor biopsy WSI is created and annotated as described herein. At block 630, a ground truth mask is generated from an .xml file. At block 640, tiles are extracted with 90% tissue. At block 650, the color is normalized. At block 660, the data is augmented (i.e., rotate and flip).

To generate the ground truth mask at block 630, PIL and Extensible Mark Up Language ("XML") processing libraries are used to plot the XML vertices, drawing a polygon on a transparent image. Due to the size of each WSI and ground truth mask, partitioning of the original image into tiles increases the dataset size, enables parallel preprocessing of images, and decreases network training time for parameters. In addition, at block 640, extracting images from the highest level of magnification (for example, 40×) allows for the greatest level of detail and resolution. Therefore, patches of 512×512 pixels at 40× resolution are extracted from both the WSI and ground truth mask using PIL.

At block 650, a simple normalization technique decreases the dataset variation from interfering with the training of the network and increases contrast within the tiles. A mean color is computed over the image and subtracted from each pixel. This normalizes each WSI and ensures tissue preparation, staining, and imaging invariance.

Image augmentation is used to increase the size of the dataset and promote rotational invariance. Specifically, at block 660, each tissue patch is rotated in 90 degree increments and reflected horizontally and vertically, to result in a six fold increase in the training data.

Additional extensive preprocessing steps are avoided because the neural networks' large number of feature maps and network parameters allow the networks to learn the appropriate steps that may be applied.

Tumor Feature Segmentation

The first task in the overall data processing pipeline, tumor feature segmentation, classifies the relevant tumor and necrosis regions in the patched WSI. The tumor feature segmentation classifier assigns a tissue region label from FIG. 2A at table 200 to every pixel in the image.

Figure 8:
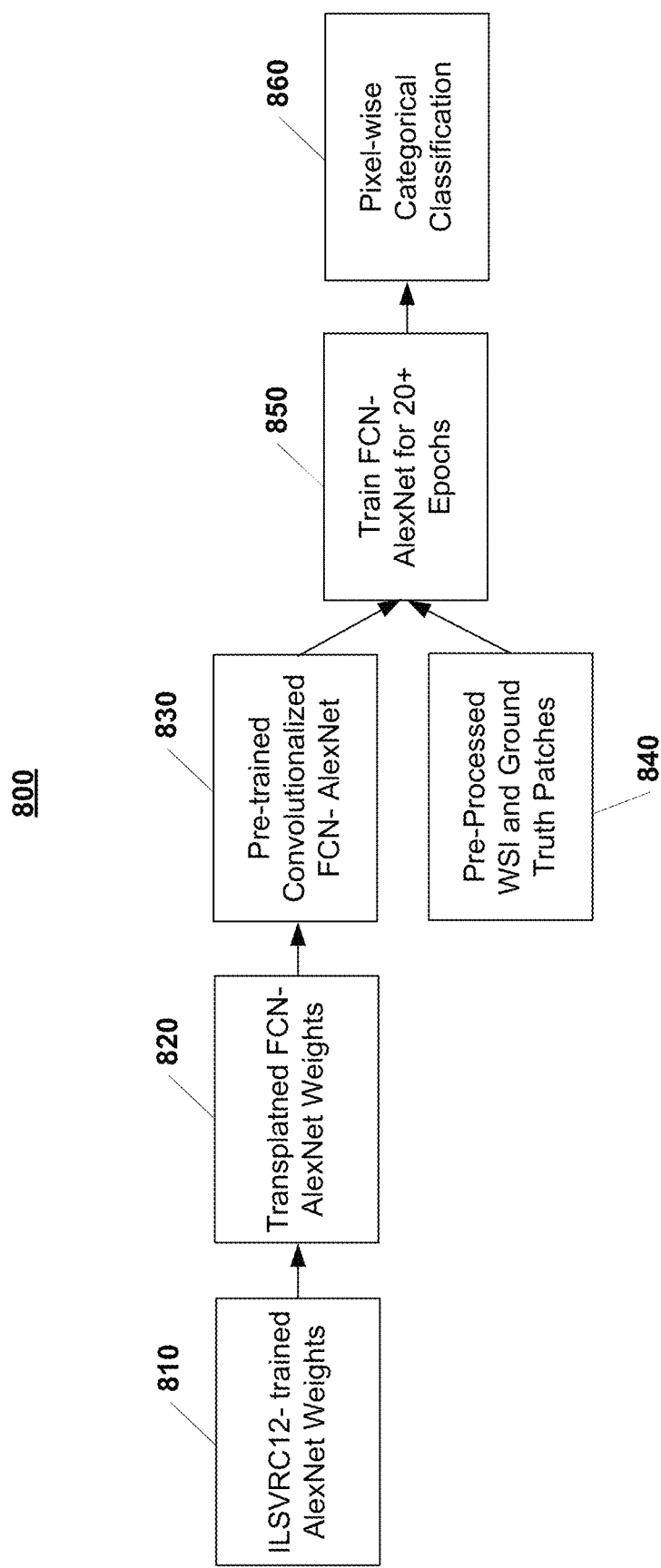
FIG. 8 depicts a flowchart of the tumor feature segmentation classifier according to an exemplary embodiment.

The tumor feature segmentation classifier, may be a semantic segmentation neural network, adapted from a classification neural network, with a data flowchart as shown in FIG. 8 at 800. In the flow 800, at block 810, trained AlexNet weights are used. At block 820, FCN AlexNet weights are transplanted. At block 830, convolutionized FCN-AlexNet weights are pre-trained. At block 840, WSI and ground truth patches are pre-processed. At block 850, AlexNet is trained for at least 20 epochs. At block 860, a pixel-wise categorical classification is performed. This flow is described below.

Exemplary embodiments rely upon an adaptation of AlexNet as the network architecture used to classify the patched WSI. In the semantic segmentation neural network, each pixel in the image is assigned a category, as opposed to assigning the entire image to a category. AlexNet was chosen due to its high-ranking performance in the 2012 ImageNet Large Scale Visual Recognition Challenge (ILSVRC). AlexNet was chosen due to its simplistic 8-layer structure, which made it ideal for adapting to this segmentation task. However, other architectures with similar capabilities and structure could also be used.

AlexNet architecture, as used by exemplary embodiments, is a CNN of eight layers having two major parts: a feature extractor and a classifier. The feature extraction part consists of five convolutional layers, which are used to extract abstract and complex features. The classifier part consists of three fully-connected layers, which learn the relationships between extracted features to produce a global classification of the image.

A Caffe Net Surgery script was written to transfer weights from the ImageNet-trained AlexNet CNN to newly the constructed FCN-AlexNet.

Training the CNN from scratch using random initialization of weights would be difficult because of the relatively limited size of training dataset (255,000 generated patches from 10 patients). Therefore, the network is initialized using the transfer learning technique, wherein knowledge from a previous learned task using a larger dataset is applied to a new task. An ImageNet dataset is chosen as an appropriate data source to transfer knowledge because of its size (consisting of over 3.2 million images), and diverse set of everyday images, including cats and trees, etcetera. Accordingly, the effective primitive edge and feature detection capabilities learned by the network can be applied to the unrelated task of identifying GBM tumor features.

The preprocessed patches are divided into three groups: training; validation; and testing. The training allotment, 70% of the total patches, is used as direct input to the network to learn the associated weights. The validation allotment, 20% of the total patches, is used to track accuracy and loss metrics for data on which the network was not previously trained. The validation information is used to determine when to stop the training process to prevent overfitting. Overfitting is a phenomenon in which a machine learning model adapts so closely to a given dataset, it is not as accurate when given the new data. Overfitting is marked by low error on training data, but high error rate on new data. Finally, the testing allotment, 10% of the total patches, is used to determine overall accuracy on never seen data.

Following the transplantation of the trained AlexNet weights into modified FCN-AlexNet, the network is fine-tuned by continuing the backpropagation process for about 20 epochs of training, during which, the segmented IVY-GAP patches pass through the network repeatedly.

In order to generate the pixel-wise classification, the CNN is modified to an FCN in two steps. First, the final three fully-connected layers are eliminated and replaced with convolutional layers. This change allows the network to process larger images (as opposed to the original 224×224 pixels) by sliding a window across the image and generating a classification per window. Second, in order to extract a refined classification, de-convolutional layers are implemented following the convolutional layers. These layers predict the input that would have generated the convolutionalized output. Finally, the adapted FCN-AlexNet makes a single classification per 32×32 pixel block.

Hyperparameters for the training process are chosen based on the future of the transfer learning technique. A low base learning rate of 0.001 may be chosen to avoid greatly distorting the pre-trained weights. In addition, a batch size of about 10 images may be chosen as the maximum allowed due to the space constraints on the GPU. A standard Stochastic Gradient Descent ("SGD") is used as a solver.

Tumor Molecular Subtype Classification

The second task in the overall data processing pipeline, tumor molecular subtype classification, has three subtypes: Classical; Mesenchymal; and Proneural, which would have been previously identified via genetic analysis of the TCGA dataset. The three tumor molecular subtypes are defined by mutations to EGFR, NF1, and PDGFRA/IDH1 genes, respectively, and respond uniquely to radiation and chemotherapy. FIG. 2C at table 275 details the types of tumors.

Figure 9:
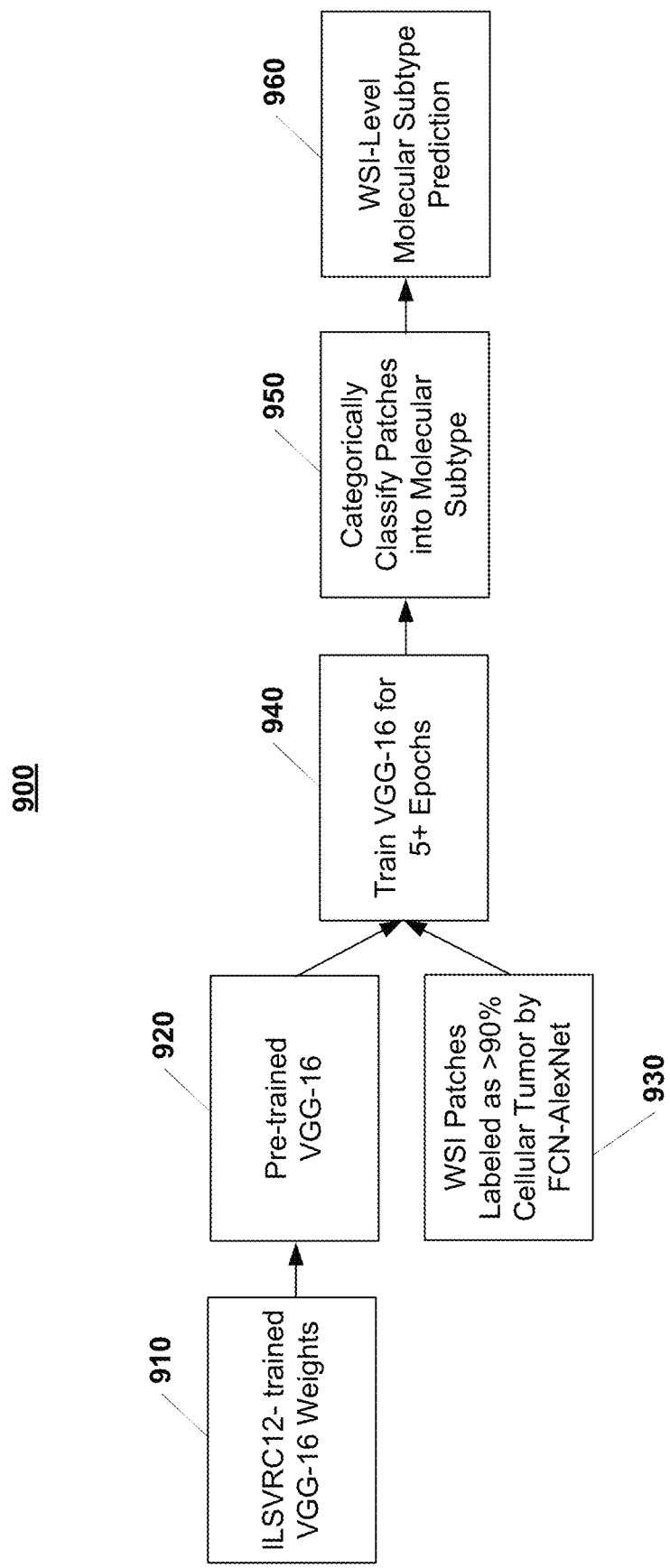
FIG. 9 depicts a flowchart of a tumor molecular subtype classifier according to an exemplary embodiment.

The flow of data for the tumor molecular subtype classification, as shown in FIG. 9 at 900, is similar to that of the tumor feature segmentation classification. The flow 900 begins at block 910 with VGG-16 weights. At block 920, the VGG-16 is pre-trained. At block 930, WSI patches are labeled by FCN-AlexNet. At block 940, VGG-16 is trained for at least five epochs. At block 950, patches are categorically classified into molecular subtype. At block 960, a WSI-level molecular subtype prediction is made.

There are two major differences between the data flow for the tumor feature segmentation classification and tumor molecular subtype classification. Instead of using patches from all parts of the WSI as done in the tumor feature segmentation classification, for the tumor molecular subtype classification only the cellular tumor regions are used in the input (block 930). The cellular tumor is chosen because it is the densest part of the tumor, with tumor cell to normal cell ratio exceeding 500:1. Additionally, CNN is used in this task because an image-wide categorical classification is required. A neural network architecture, for example VGG-16 (block 910), may be used to classify the patch. Transfer learning technique may also be used in this classification task, directly initializing learned weights from the network architecture.

The hyperparameters for the training process in tumor molecular subtype classification are similar to the hyperparameters chosen in the tumor feature segmentation classification: a low base learning rate of 0.001. In addition, a batch size of five images, and an SGD solver are chosen.

MGMT Promotor Methylation Classification

The final step in the overall processing pipeline, determining the molecular subtype and MGMT promoter methylation, classifies the methylation status of the promoter of the MGMT gene, which encodes DNA repair proteins. In GBM patients, MGMT methylation is arguably one of the most important prognostic factors because it determines treatment responses to alkylating agents, which are used to treat GBM.

Figure 10:
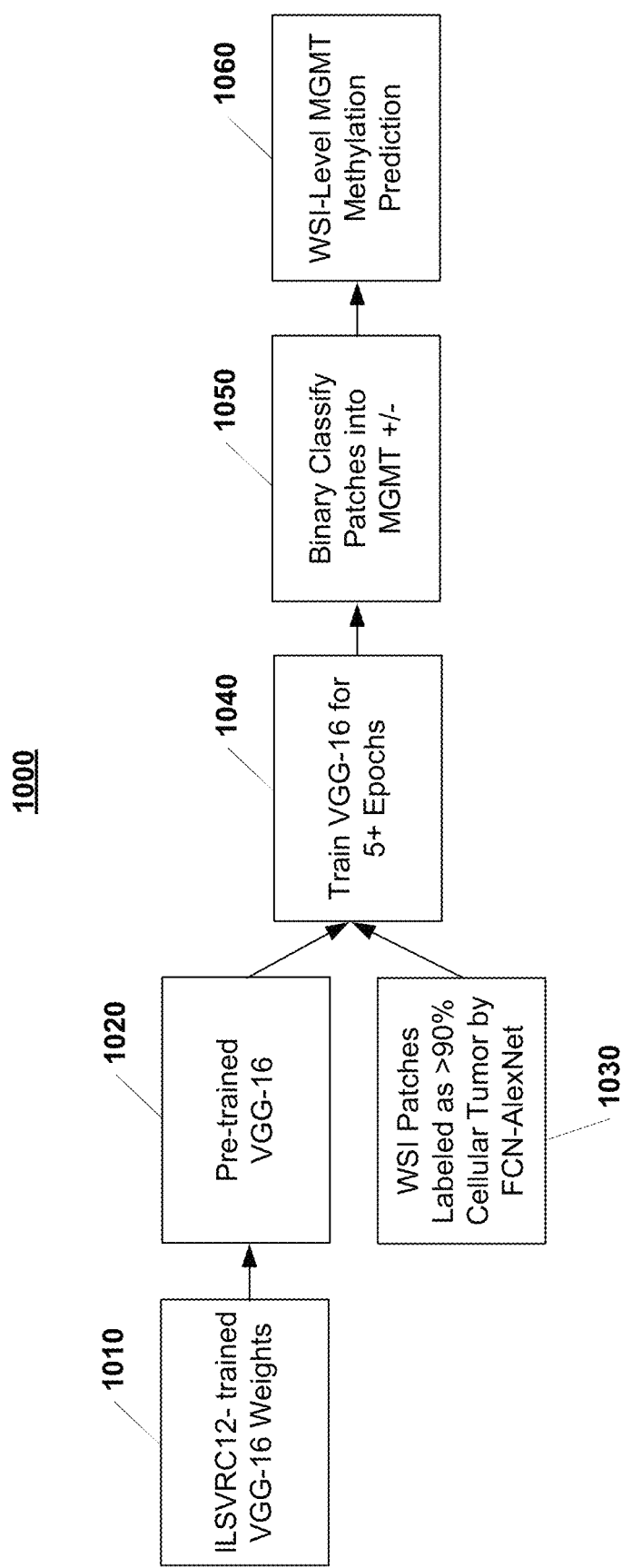
FIG. 10 depicts a flowchart of a tumor feature segmentation classifier according to an exemplary embodiment.

The flow of data for the classification of the methylation status, as shown in FIG. 10 at 1000, is very similar to the tumor molecular subtype classification. The flow 1000 begins at block 1010 with VGG-16 weights. At block 1020, the VGG-16 is pre-trained. At block 1030, WSI patches are labeled by FCN-AlexNet. At block 1040, VGG-16 is trained for at least five epochs. At block 1050, patches are binary classified in MGMT+/−. At block 1060, a WSI-level methylation prediction is made.

The flow of data for the classification of the methylation status differs because the methylation status only has two categories: MGMT+ and MGMT−. Similar hyperparameters are chosen for both the tumor molecular subtype and methylation status classification because of the similarity of the classification tasks.

EXAMPLES

Figure 11A:
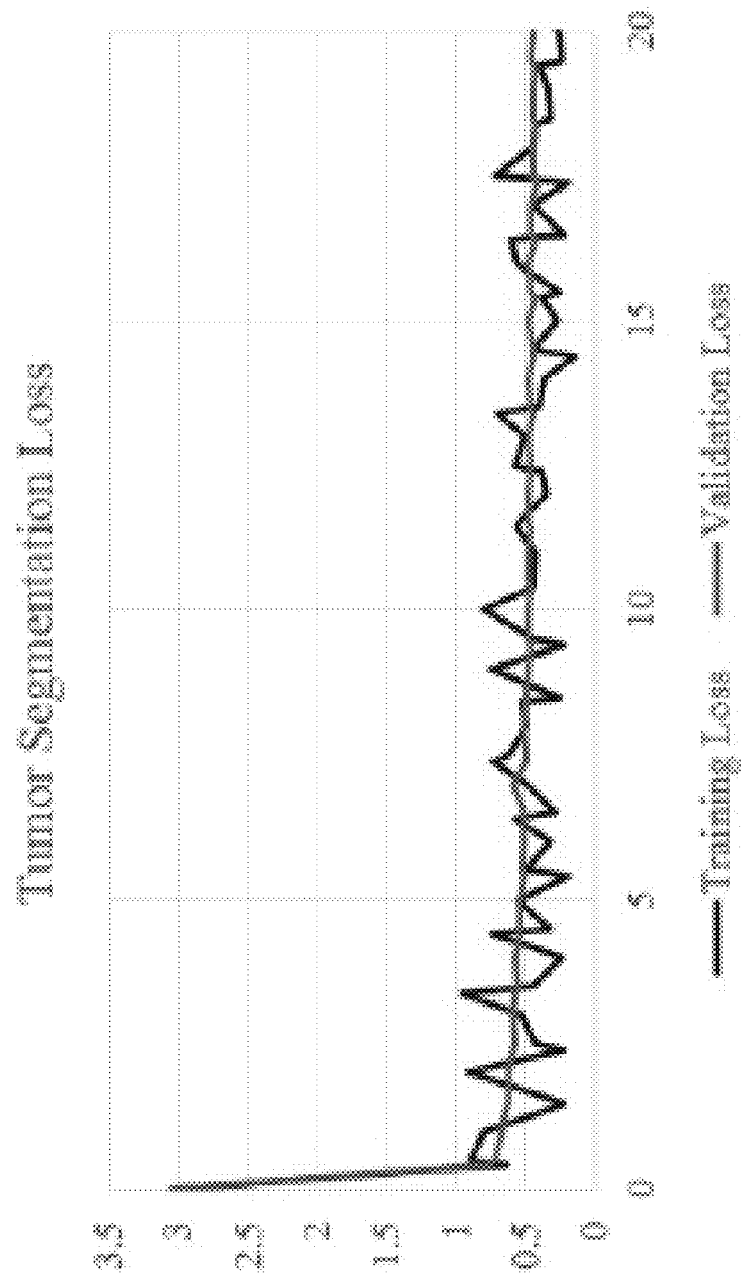
FIG. 11A depicts a graph of validation and training loss for the tumor segmentation task over a training period according to an exemplary embodiment.
Figure 11B:
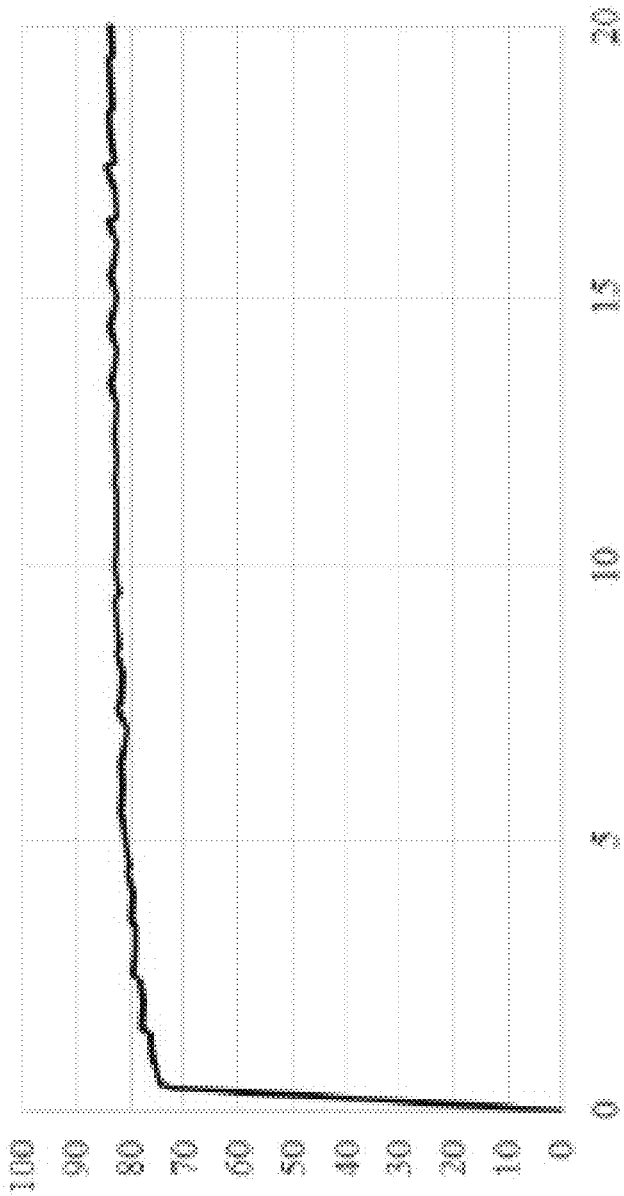
FIG. 11B depicts a graph of validation accuracy for the tumor segmentation task over a training period according to an exemplary embodiment.

Following the 20 training epochs, the tumor feature segmentation algorithm achieved a training loss of 0.438, validation loss of 0.427, and validation accuracy of 84.70%. The network achieved an accuracy of 86.02% on the test set of images. Throughout the training process, both the training and validation loss decreased significantly during the first epoch, starting at 3.024 and 3.044 respectively, and gradually decreased before leveling off in Epoch 20. Accordingly, the validation accuracy started at 0.00% and significantly increased during the first epoch before leveling off at 84.70%, as shown in the graphs of FIGS. 11A at 1100 and 11B at 1150.

Figure 12:
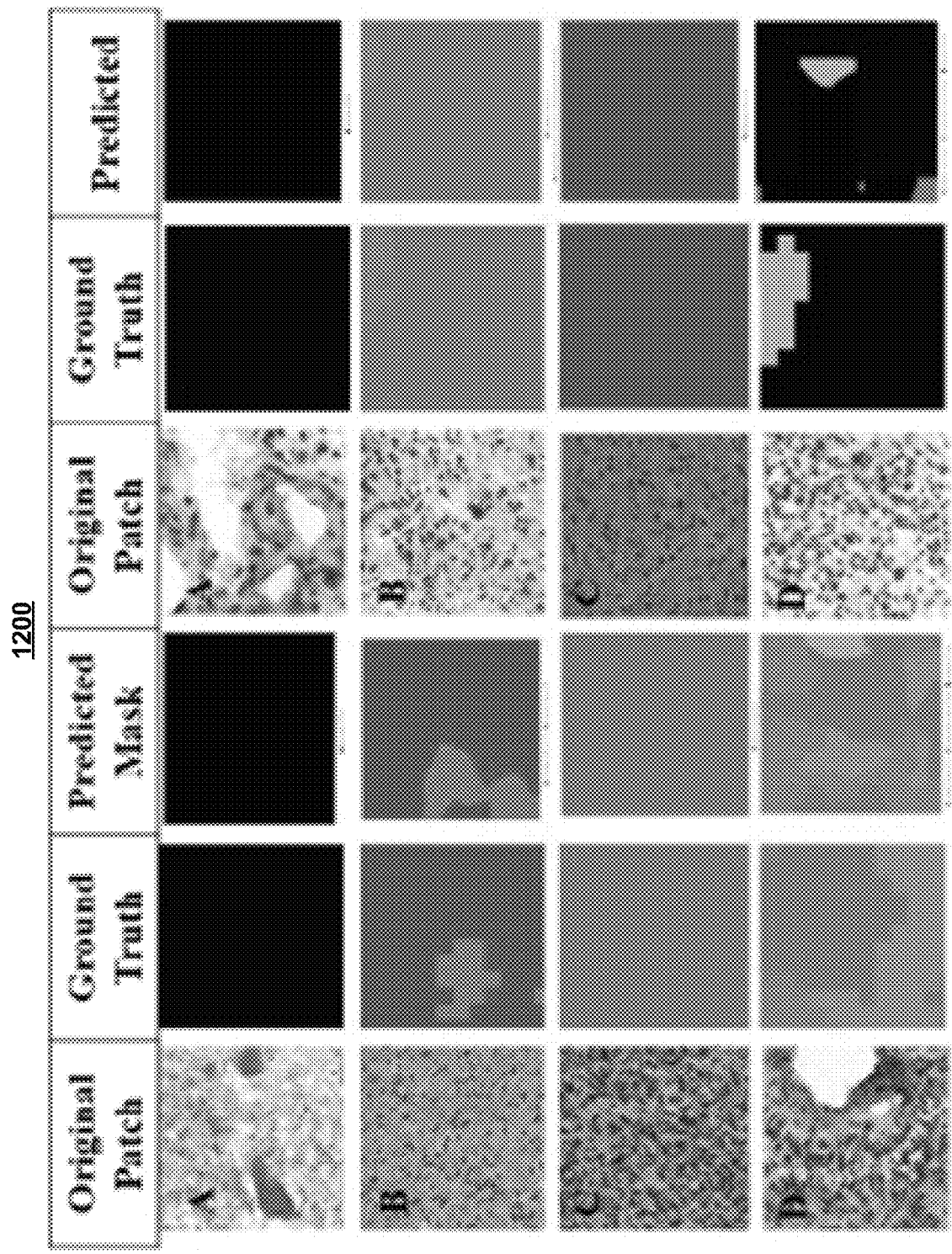
FIG. 12 depicts an example of images chosen from the test set and analyzed through the trained network according to an exemplary embodiment.

Throughout the training process, several levels of feature segmentation were achieved, as shown in FIG. 12 at the table 1200. They are as follows:

Stage A (epoch 1): High accuracy was achieved in classification of single-tissue tiles of the necrosis class. From a biological standpoint, this result was expected, as necrosis tissue is easily distinguishable from tumor tissue in the color and density of cells.

Stage B (epoch 3): Accuracy began to improve with mixed two-tissue tiles. Surprisingly, this result was achieved prior to the accurate classification of single-tissue tiles of other classes.

Stage C (epoch 9): High accuracy was achieved with other types of single-tissue tiles such as infiltrating and cellular tumor.

Stage D (epoch 13): The network demonstrates improved accuracy on structurally difficult multi-tissue tiles and achieves high accuracy in determining types of tissue present in a tile.

The weights of the model were fine-tuned to attain an improved performance on the training and validation sets while still general enough to accurately assess a new test set. This claim of minimal overfitting is supported by the minimal discrepancy between the training and validation loss values and high test accuracy percentage.

Figure 13:
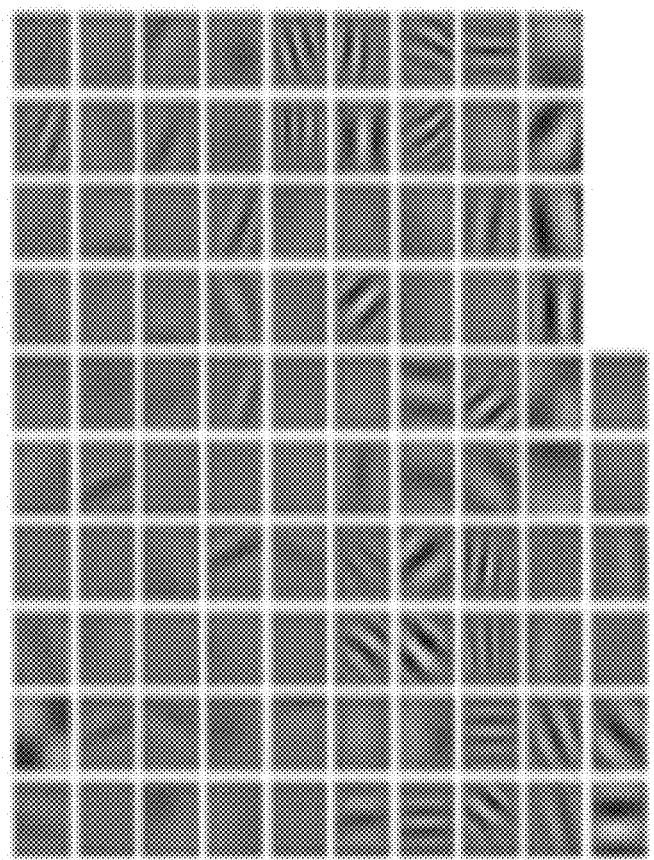
FIG. 13 depicts weights learned by the first convolutions layer of the trained FCN-AlexNet network according to an exemplary embodiment.

FIG. 13 at 1300 offers a visual representation of the first layer kernal weights learned by the network. As demonstrated by the image, the network learned low-level morphological features such as edges and the blue/purple colors associated with pathology images and their color complements. Together, these learned features may be used to recognize nuclei and inter- and intra-nuclear spaces and offer qualitative support for the network's quantitative performance.

Figure 14A:
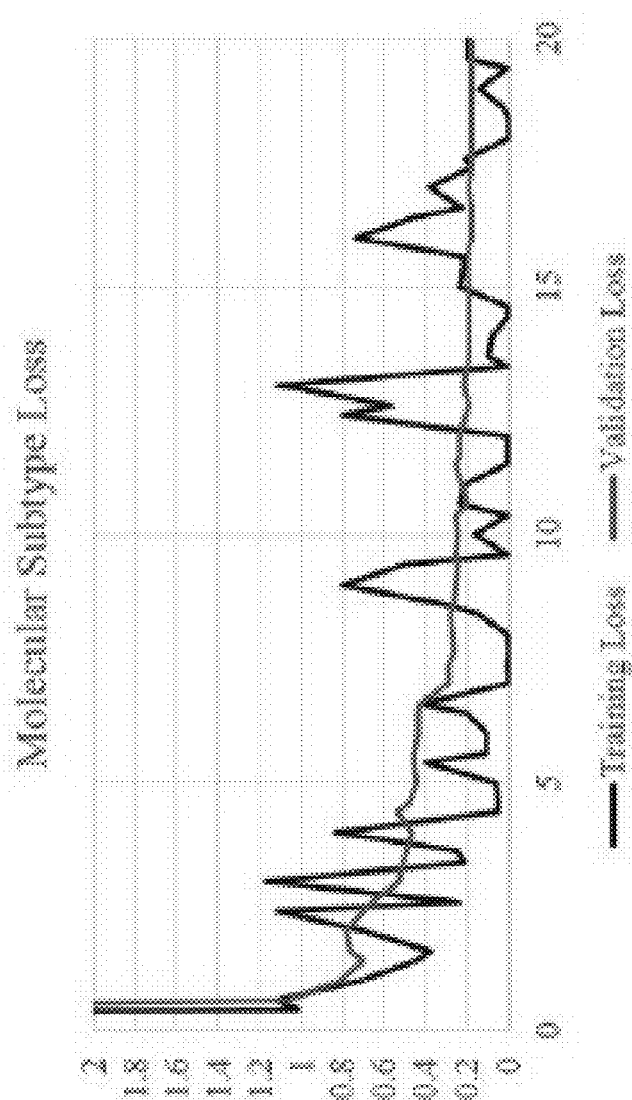
FIG. 14A depicts a graph of validation and training loss for the molecular subtype classifier over a training period according to an exemplary embodiment.
Figure 14B:
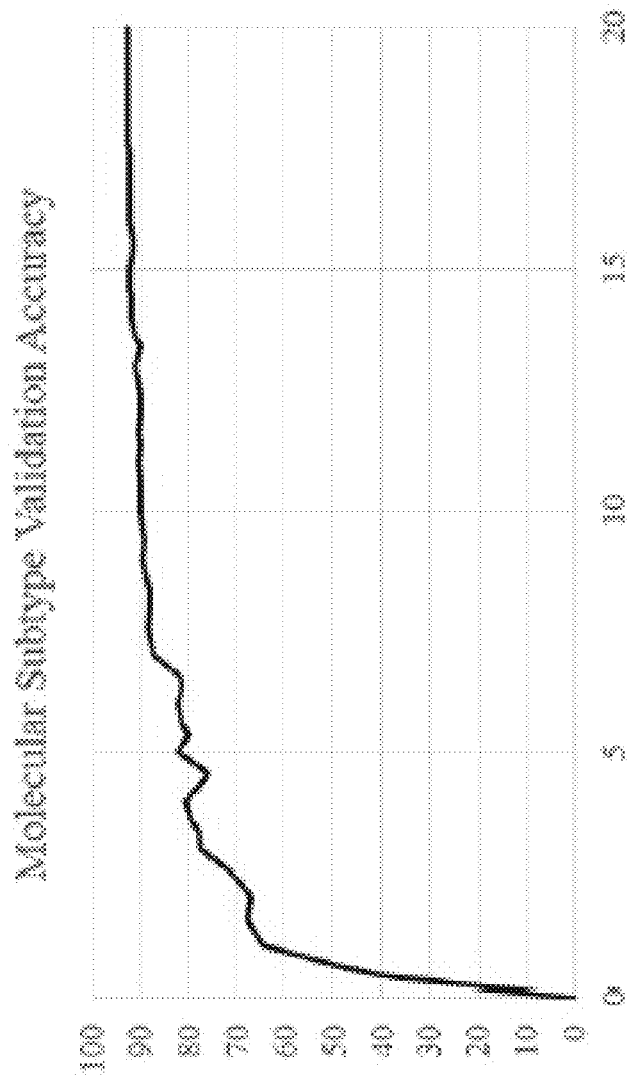
FIG. 14B depicts a graph of validation accuracy for the molecular subtype classifier over a training period according to an exemplary embodiment.

Following 12 training epochs, the tumor subtype classifier reached a validation accuracy of 92.60%, validation loss of 0.177, training loss of 0.201. The patch-level calculated accuracy on the test set was 93.21%. Of the total 30 test set WSIs, the correct tumor subtype was predicted on a WSI-level 100% of the time. Similar to the tumor feature segmentation classifier, the training and validation loss were initially very large (18.797 and 16.677, respectively) and decreased rapidly in the first epoch before leveling off. The validation accuracy, which began at 0%, rapidly increased in the first few epochs before leveling off, especially when the learning rate was decreased by 10% after epoch 8. This is shown in FIGS. 14A at 1400 and 14B at 1450.

$$\text{Sensitivity} = \frac{TP}{TP+FN} * 100, \text{Sensitivity} = \frac{TN}{TN+FP} * 100$$

The sensitivity and specificity of the test classification was calculated using the formulas above using the true positives (TP), false negatives (FN), false positives (FP), and true negatives (TN). The classifier obtained a sensitivity of 93.846% percent, 96.154%, 94.839%, and 88.092%; and specificity of 94.904%, 95.784%, 99.843%, and 99.221% percent, for the mesenchymal, classical, proneural, and neural subtypes, respectively. These statistics are summarized in Table 4.

Figure 15A:
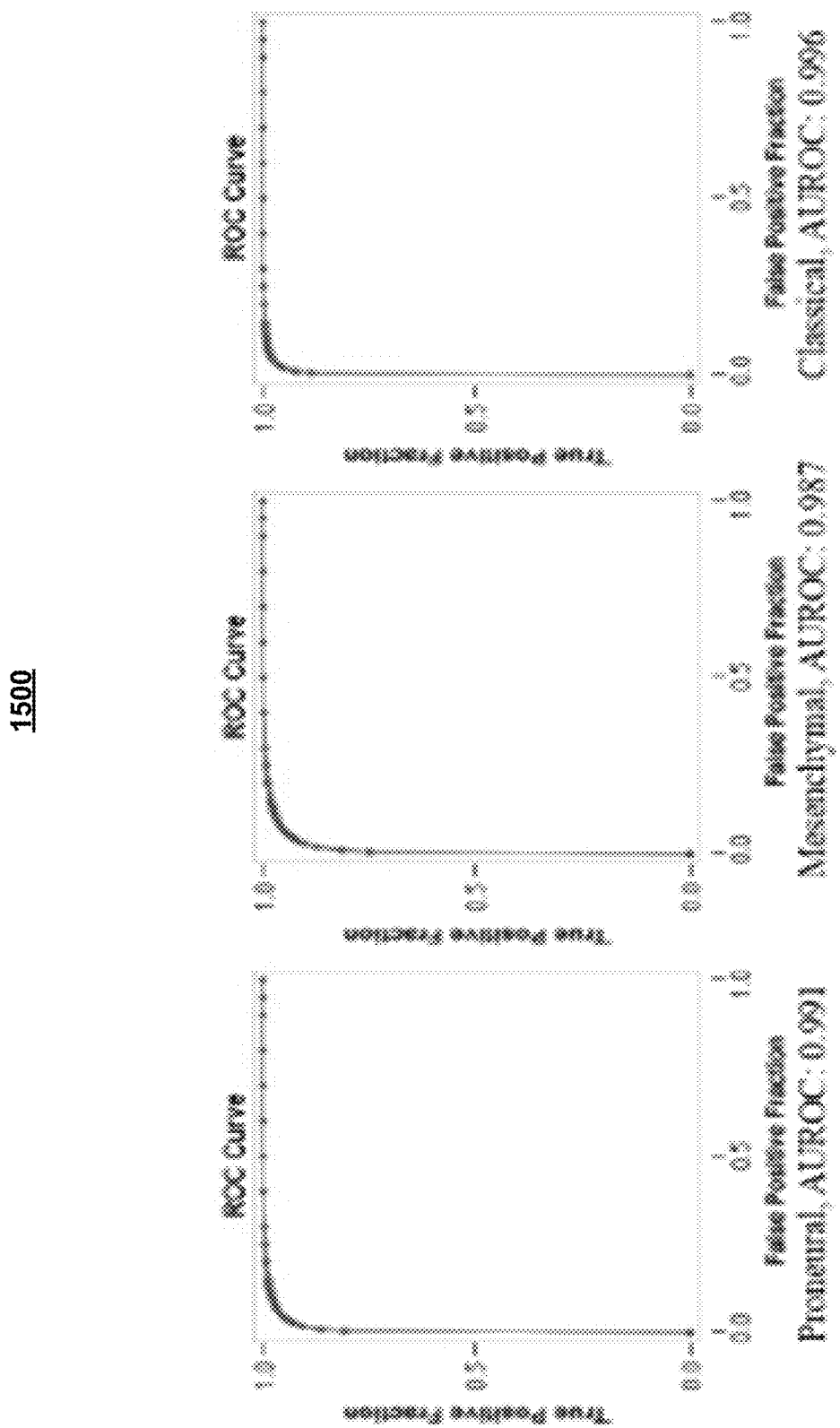
FIG. 15A depicts a graph of Receiver Operating Characteristic ("ROC") curves and Area Under the Receiver Operating Characteristic curve ("AUROC") values for each of three molecular subtypes in an all-or-nothing scheme according to an exemplary embodiment.
Figure 15B:
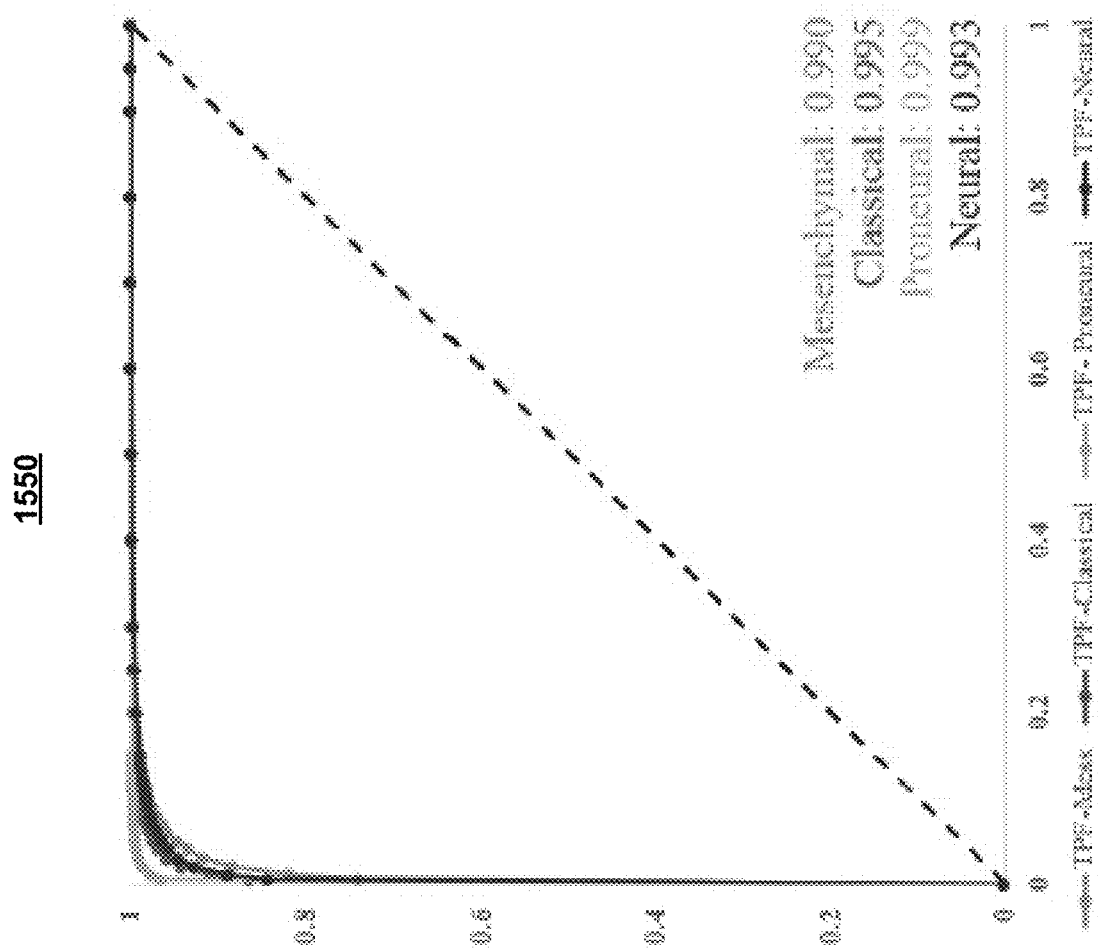
FIG. 15B depicts a second graph of ROC curves and AUROC values for each class in an all-or-nothing scheme according to an exemplary embodiment.

The Receiver Operating Characteristic ("ROC") curve represents more holistic representation of the results than the combination of percent accuracy, sensitivity, specificity, and loss functions, and is a commonly used metric in evaluating medical decision making algorithms. The x-axis represents the false positive rate, while the y-axis is the true positive rate. The curve is then plotted over variable threshold values, and the area under the curve ("AUROC") is taken as a common metric. An ROC curve with a random classifier would be the line y=x, resulting in an AUROC of 0.5. A perfect classifier, on the other hand, would have an ROC curve that intersects the point (0, 1), and would thus have an AUROC of 1.0. Due to the nature of a multi-class classification, a single ROC curve does not fully represent the classifier. FIG. 15A at 1500 depicts ROC curves. Therefore, ROC curves were plotted for each class in an all-or-nothing fashion, as shown in FIG. 15B at 1550.

Figure 16:
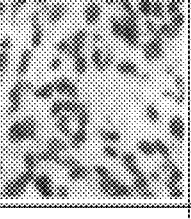
FIG. 16 depicts an example of images chosen from the test set and analyzed through the trained network, in which C represents the Classical subtype, M represents the Mesenchymal subtype, and P represents Proneural subtype and the bolded percentage is the ground truth value according to an exemplary embodiment.
Figure 17:
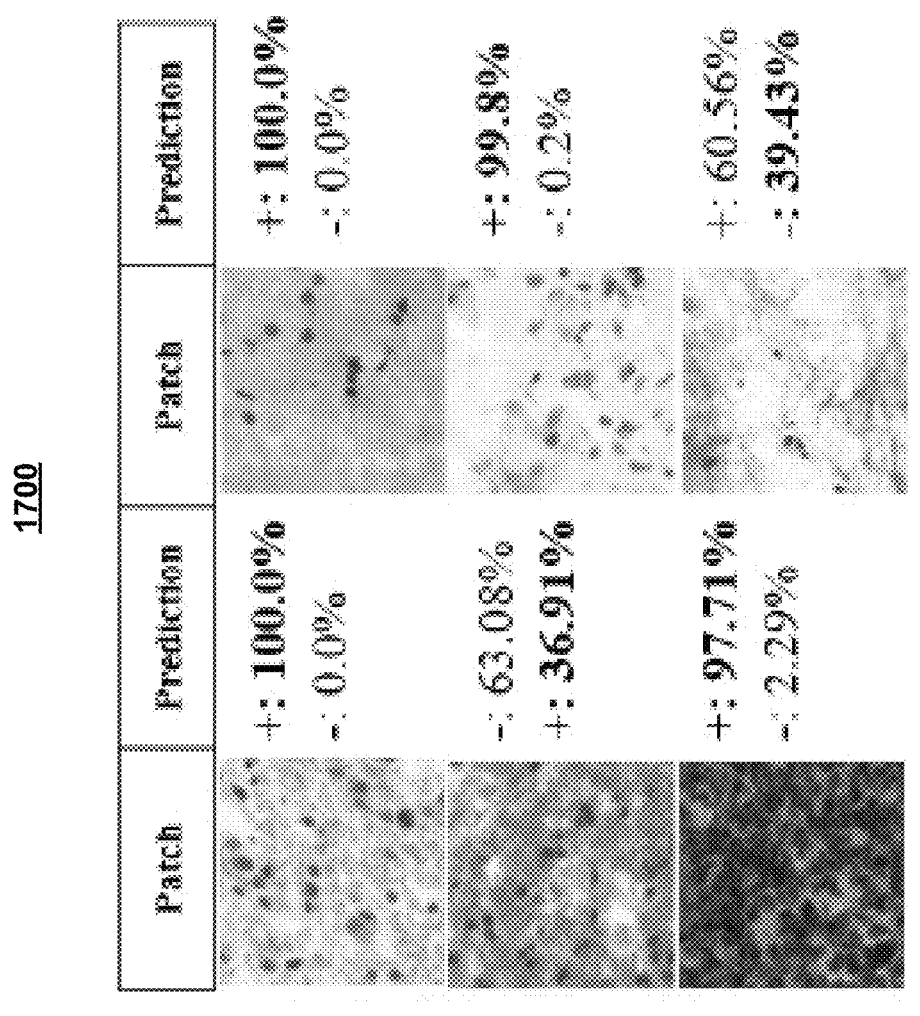

FIG. 16 at table 1600 displays twelve patches from the test set and associated percent confidence values for each category according to an exemplary embodiment. The overall classification of the image was chosen as the class with the highest percent confidence value. The first row represents misclassified patches, while the other two rows depict correctly predicted tiles. FIG. 17 at 1700 provides another depiction of six patches according to another exemplary embodiment. The overall classification of the image was chosen as the class with the highest percent confidence value.

Figure 18A:
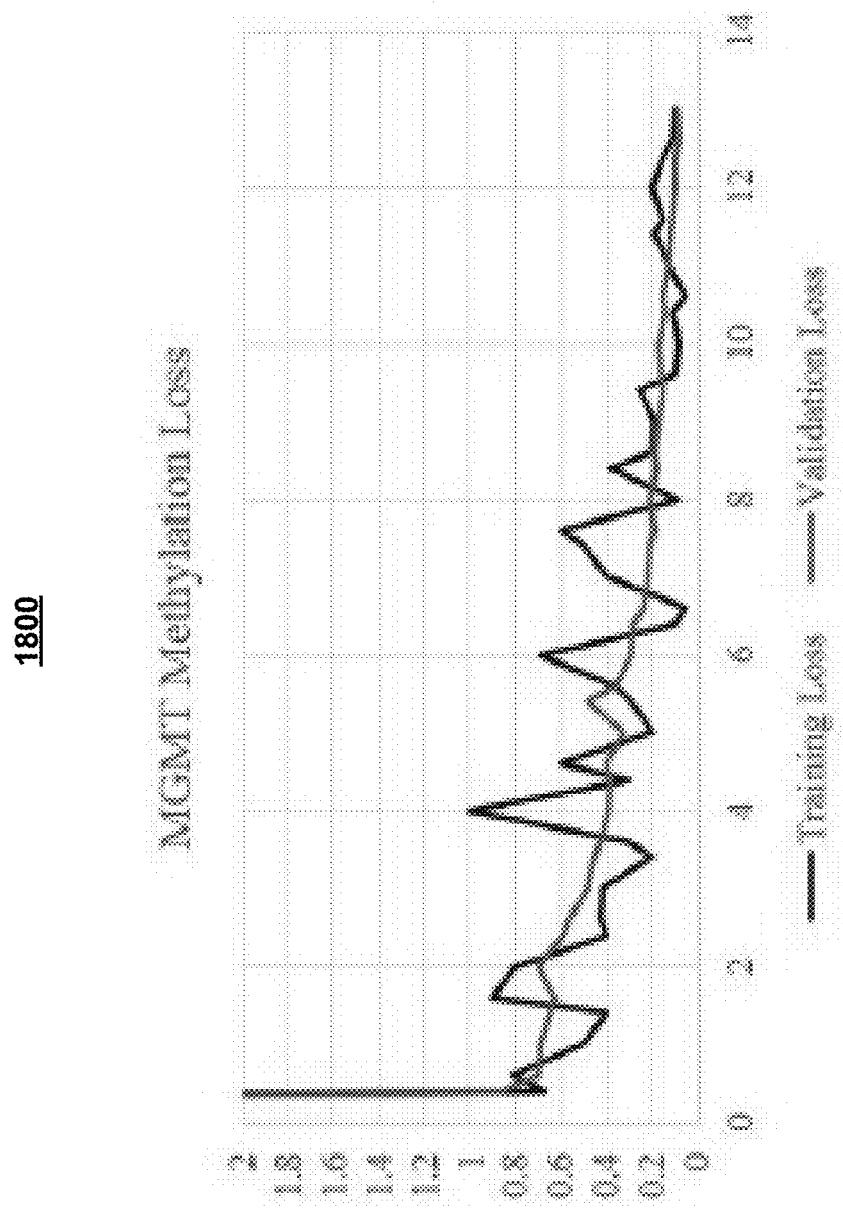
FIG. 18A depicts a graph of validation and training loss over a 13-epoch training period according to an exemplary embodiment.
Figure 18B:
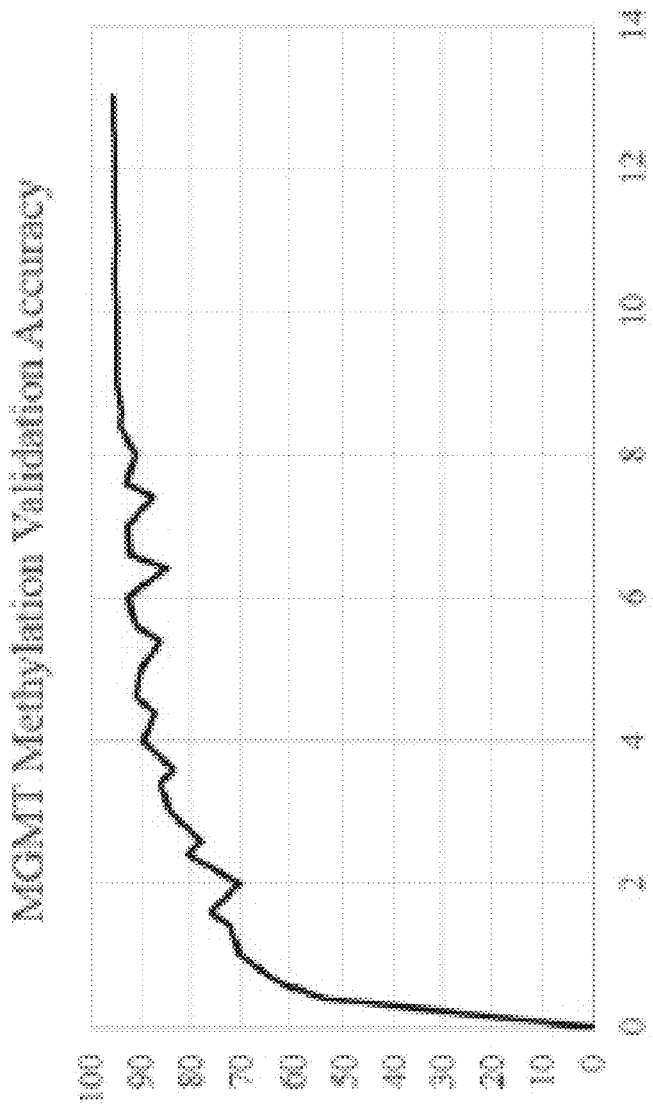
FIG. 18B depicts a graph of validation accuracy over a 13-epoch training period according to an exemplary embodiment.

Following 13 training epochs, the tumor subtype classifier reached a validation accuracy of 95.57%, validation loss of 0.092, training loss of 0.102, as shown in FIGS. 18A at 1800 and 18B at 1850. The patch-level calculated accuracy on the test set was 96.00%. The achieved sensitivity and specificity on the test set was 89.42% and 91.12%, respectively. Of the total 30 testing WSIs, the MGMT promoter methylation status was predicted correctly on a WSI-level 100% of the time. The training loss and validation loss began at 20.416 and 13.706 respectively, and the validation accuracy began at 0%. Similar to the molecular subtype classifier, the accuracymetric rapidly increased in the first few epochs while the loss metrics rapidly decreased, as shown in FIGS. 18A and 18B. Because the classification task was binary in nature, only one ROC was plotted, with an AUROC of 0.96.

FIG. 19 at table 1900 compares exemplary embodiments to existing studies, specifically: Levner, I., Drabycs, S., Roldan, G., Robles, P. D., Cairncross, J., & Mitchell, R. (2009). Predicting MGMT methylation status of glioblastomas from MRI texture. *Medical image computing and computer-assisted intervention*; Hou, L., Samaras, D., Kurc, T., Gao, Y., Davis, J., & Saltz, J. (2016). Patch-based convolutional neural network for whole slide tissue image classification. *arXiv*; Homeyer, A., Schenk, A., Arlt, J., Dahmen, U., Dirsch, O., & Hahn, H. (2013). Practical quantification of necrosis in histological whole-slide images. *Computerized medical imaging and graphics.*

While previous studies have segmented pertinent regions of interest, none have isolated the same number of diagnostically-relevant regions that exemplary embodiments, such as GlioVision, have. Exemplary embodiments have surpassed the accuracy of previous MGMT prediction studies.

Several calculated metrics, summarized in FIG. 20 at 2000, all point towards the validity of exemplary embodiments when applied to a set of new testing data and reinforce the usability of the system in a clinical setting.

All publications, patents, and published patent applications mentioned in this specification are herein incorporated by reference, in their entirety, to the same extent as if each individual publication, patent, or published patent application was specifically and individually indicated to be incorporated by reference.

It will be readily understood by those persons skilled in the art that the various embodiments are susceptible to broad utility and application. Many embodiments and adaptations other than those herein described, as well as many variations, modifications and equivalent arrangements, will be apparent from or reasonably suggested by the various embodiments and foregoing description thereof, without departing from the substance or scope of the various embodiments.

Accordingly, while the various embodiments have been described here in detail in relation to its exemplary embodiments, it is to be understood that this disclosure is only illustrative and exemplary of the various embodiments and is made to provide an enabling disclosure of the various embodiments. Accordingly, the foregoing disclosure is not intended to be construed or to limit the various embodiments or otherwise to exclude any other such embodiments, adaptations, variations, modifications or equivalent arrangements.

What is claimed is:

1. A computer implemented method for characterization of a brain tumor comprising:
   receiving, on at least one processor, data from a subject with a brain tumor;
   evaluating, using the at least one processor, the data using a classifier which is an electronic representation of a classification system, each said classifier trained using an electronically stored set of training data vectors, each training data vector representing an individual human and data for the respective human, each training data vector further comprising a classification with respect to the characterization of the brain tumor in the respective human, wherein the classification system comprises a Fully Convolutional Network (FCN), Convolutional Neural Network (CNN), or an ensemble thereof, and wherein the characterization comprises identification of the tumor as a glioblastoma multiforme (GBM), and the characterization further comprises providing tumor features, O6-methylguanine-DNA methyltransferase (MGMT) methylation status, molecular subtype determination, or combinations thereof; and
   outputting, using the at least one processor, a classification of the sample from the human test subject concerning the characterization of the brain tumor in the subject based on the evaluating step.

2. The method of claim 1, wherein the classification system is further selected from the group consisting of support vector machines, genetic algorithms, penalized logistic regression, LASSO, ridge regression, naive Bayes classifiers, classification trees, k-nearest neighbor classifiers, neural nets, elastic nets, Bayesian neural networks, Random Forests, gradient boosting trees, AdaBoost, or an ensemble thereof.

3. The method of claim 1, wherein the data comprises histopathological data, genetic information, or a combination thereof.

4. The method of claim 3, wherein the histopathological data is obtained from a whole brain slide comprising at least a scanned biopsy Whole Slide Image (WSI) of a human brain of a subject having a brain tumor.

5. The method of claim 3, wherein the histopathological data comprises leading edge (LE), infiltrating tumor (IT), cellular tumor (CT), perinectronic zone (CTpnz), necrosis (CTne), pseudopalisading cells (CTpan), hyperplastic blood vessels (hbv), or a combination thereof.

6. The method of claim 3, wherein the genetic information comprises changes in EGFR, NF1, PDGFRA/IDH1, and cancer implicated genes and the changes comprise mutations.

7. The method of claim 6, wherein the genetic information comprises chromosome 7, amplification chromosome 10 deletion, high-level EGFR amplification, deletions in NF1 gen, high expression of CH13L1 gene, high expression of MET gene, alternations of PDFRA gene, point mutations in IDH1, TP53 mutation, expression of neuron markers by astrocytes, mutations in oncogenes, (MGMT) methylation, or a combination thereof.

8. The method of claim 7, wherein the neuron markers comprise NEFL, GABA Receptor $\alpha 1$, SYT1, SLC12A5.

9. The method of claim 1, wherein the characterization further comprises a molecular subtype classification as a Classical, Mesenchymal, Proneural, or Neural glioblastoma.

10. The method of claim 1, wherein the characterization further comprises that the GBM is either MGMT+ OR MGMT−.

11. The method of claim 1, wherein the characterization further comprises providing histopathological data that composes leading edge (LE), infiltrating tumor (IT), cellular tumor (CT), perinectronic zone (CTpnz), necrosis (CTne), pseudopalisading cells (CTpan), hyperplastic blood vessels (hbv), or a combination thereof.

12. The method of claim 1, wherein the test data and each training data vector further comprises at least one additional characteristic selected from the group consisting of the sex, age, genetic information, biomarker data, smoking status, medical history or a combination thereof of the individual human.

13. A non-transitory computer readable medium storing an executable program comprising instructions to perform the method of claim 1.

14. A computer implemented method, comprising:
receiving, by a computer processor, a scanned biopsy WSI of a human brain of a subject having a brain tumor wherein the computer comprises a cloud-based server and wherein the scanned biopsy WSI is received through a web-based application;
preprocessing, by a computer, the scanned biopsy WSI;
processing, by the computer, the preprocessed scanned biopsy WSI using one or more machine learning architectures;
outputting, by the computer through the use of one or more trained machine learning architectures, an annotated image, wherein the annotated image comprises tumor feature segmentation, a subtype of the tumor, and a O6-methylguanine-DNA methyltransferase (MGMT) promotor methylation status; and
giving a capability, through the annotated image, to determine a personalized treatment plan for the subject with glioblastoma multiforme (GBM) based on the tumor's subtype and the MGMT promotor methylation status.

15. The method of claim 14, wherein the one or more trained machine learning architectures are trained neural networks, wherein the one or more trained neural networks comprise one network for each classification task.

16. A non-transitory computer readable medium storing an executable program comprising instructions to perform the method of claim 14.

17. A system, comprising:
a server comprising at least one processor and memory comprising non-transitory computer-readable instructions which when executed by the processor cause the processor to perform the steps comprising:
receiving a scanned biopsy whole side image (WSI) of a human brain of a subject having a brain tumor comprising a Gliobastoma Multiforme (GBM) from a computer terminal that is located remotely from the server;
preprocessing the scanned biopsy WSI by applying a tile-based image analysis framework to the scanned biopsy WSI;
processing the preprocessed scanned biopsy WSI using three trained neural networks compromising one trained neural network for tumor features, one trained neural network for tumor subtype, and one trained neural network for O6-methylguanine-DNA methyltransferase (MGMT) promoter methylation status; and
outputting an annotated image, wherein the annotated image comprises smaller patches, a subtype of the tumor, and the MGMT promotor methylation status as MGMT+ or MGMT−.

* * * * *

UNITED STATES PATENT AND TRADEMARK OFFICE
CERTIFICATE OF CORRECTION

PATENT NO. : 10,748,040 B2  
APPLICATION NO. : 16/193828  
DATED : August 18, 2020  
INVENTOR(S) : Kopparapu Page 1 of 1

It is certified that error appears in the above-identified patent and that said Letters Patent is hereby corrected as shown below:

In the Claims

In Claim 7, Column 25, Line 27, "(MGMT) methylation," should read --MGMT methylation,--.

In Claim 11, Column 25, Lines 38-39, "composes" should read --comprises--.

Signed and Sealed this  
Twenty-seventh Day of August, 2024

Katherine Kelly Vidal  
*Director of the United States Patent and Trademark Office*